United States Patent [19]

Milich et al.

[11] Patent Number: 4,599,230
[45] Date of Patent: Jul. 8, 1986

[54] SYNTHETIC HEPATITIS B VIRUS VACCINE INCLUDING BOTH T CELL AND B CELL DETERMINANTS

[75] Inventors: David R. Milich, San Diego; Frank V. Chisari, Del Mar, both of Calif.

[73] Assignee: Scripps Clinic and Research Foundation, La Jolla, Calif.

[21] Appl. No.: 588,122

[22] Filed: Mar. 9, 1984

[51] Int. Cl.⁴ .................... A61K 39/29; C07K 7/06; C07K 7/08; C07K 7/10
[52] U.S. Cl. ........................... 424/89; 424/88; 514/13; 514/14; 514/15; 514/16; 530/806; 530/324; 530/326; 530/327; 530/328
[58] Field of Search .................. 424/89, 88; 260/112.5 R; 514/13, 14, 15, 16

[56] References Cited

U.S. PATENT DOCUMENTS

| | | | |
|---|---|---|---|
| 4,415,491 | 11/1983 | Vyas | 260/112.5 R |
| 4,428,941 | 1/1984 | Galibert et al. | 260/112.5 R |
| 4,483,793 | 11/1984 | Vyas | 260/112.5 R |

FOREIGN PATENT DOCUMENTS

| | | | |
|---|---|---|---|
| 1108058 | 9/1981 | Canada | 167/130 |
| 0038765 | 4/1980 | European Pat. Off. | |
| 0044710 | 1/1982 | European Pat. Off. | 260/112.5 R |
| 0056249 | 7/1982 | European Pat. Off. | 260/112.5 R |
| 0082789 | 6/1983 | European Pat. Off. | 260/112.5 R |
| 0119342 | 9/1984 | European Pat. Off. | 260/112.5 R |
| 84/03564 | 9/1984 | PCT Int'l Appl. | |
| 84/03506 | 9/1984 | PCT Int'l Appl. | 260/112.5 R |

OTHER PUBLICATIONS

Chem. Abstr., vol. 101, p. 108574 (1984).
Chem. Abstr., vol. 101, p. 108640 (1984).
Chem. Abstr., vol. 101, p. 88513 (1984).
Chem. Abstr., vol. 99, 3895 (1983).
The Lancet (1984) 184–187, Brown, et al.
Nature, vol. 282, (1979) 575–582.
Mod. Approaches Vaccines: Mol. Chem. Basis Virus, Virulence Immun. (1983).
Proc. Nat'l Acad. Sci., 79, 4400–4404 (1982).
Proc. Nat'l Acad. Sci., vol. 80, 2365–69 (1983).
The Journal of Invest., 83, 112s–115s (1984).

*Primary Examiner*—Delbert R. Phillips
*Attorney, Agent, or Firm*—Dressler, Goldsmith, Shore, Sutker & Milnamow, Ltd.

[57] ABSTRACT

Chemically synthesized polypeptides include amino acid residue sequences that substantially correspond to the amino acid residue sequences of T cell and B cell determinant portions of a natural, pathogen-related protein, in particular, a hepatitis B virus surface antigen (HBsAg). When administered to a host alone, as polymers or as carrier-bound conjugates, the polypeptides induce the proliferation of thymus-derived cells in hosts primed against hepatitis B virus.

19 Claims, 4 Drawing Figures

```
                    20                    40                    60                    80
                     .                     .                     .                     .
MENITSGFLGPLLVLQAGFFLLTRILTIPQSLDSWWTSLNFLGGTTVCLGQNSQSPTSNHSPTSCPPTCPGYRWMCLRRF
   ├────3────┤   ├────4────┤  ├──────5──────┤
                                      ├──5a──┤
                                         ├──────────────1──────────────▶
```

```
                   100                   120         49n         140                   160
                     .                     .   ┌──────────┐        .                     .
                                              49
IIFLFILLLCLIFLLVLLDYQGMLPVCPLFPGSSTTSTGPCRTCMTTAQGTSMYPSCCCTKPSDGNCTCIPIPSSWAFGK
◀─┤      ├────6────┤          J  T      K  T  P  N  F              ├──┤
  1                           ├──────────72──────────┤                  ├──2──┤
                                                ├──72a──┤           ├──71──┤
                              ├────────────73────────────┤
```

```
                   180                   200                   220
                     .                     .                     .
FLWEWASARFSWLSLLVPFVQWFVGLSPTVWLSVIWMMWYWGPSLYSILSPFLPLLPIFFCLWVYI
```

FIG. 1

| | |
|---|---|
| Peptide 1 | (48-81) |

(48) (60)
CysLeuGlyGlnAsnSerGlnSerProThrSerAsnHis
(70)
SerProThrSerCysProProThrCysProGlyTyr
(81)
ArgTrpMetCysLeuArgArgPheIle

| | |
|---|---|
| Peptide 5 | (38-52) |

(38) (52)
SerLeuAsnPheLeuGlyGlyThrThrValCysLeuGlyGlnAsn

| | |
|---|---|
| Peptide 5a | (47-52) |

(47) (52)
ValCysLeuGlyGlnAsn

| | |
|---|---|
| Peptide 6 | (95-109) |

(95) (109)
LeuValLeuLeuAspTyrGlnGlyMetLeuProValCysProLeu

| | |
|---|---|
| Peptide 49 | (110-137) |

(110) (120)
PheProGlySerSerThrThrSerThrGlyProCysArgThrCys
(130) (137)
MetThrThrAlaGlnGlyThrSerMetTyrProSerCys

| | |
|---|---|
| Peptide 49a | (125-137) |

(125) (137)
MetThrThrAlaGlnGlyThrSerMetTyrProSerCys

| | |
|---|---|
| Peptide 71 | (140-154) |

(140) (150) (154)
ThrLysProSerAspGlyAsnCysThrCysIleProIleProSer

| | |
|---|---|
| Peptide 72 | (110-137) |

(110) (120)
IleProGlySerThrThrThrSerThrGlyProCysLysThrCys
(130) (137)
ThrThrProAlaGlnGlyAsnSerMetPheProSerCys

| | |
|---|---|
| Peptide 72a | (125-137) |

(125) (137)
ThrThrProAlaGlnGlyAsnSerMetPheProSerCys

| | |
|---|---|
| Peptide 73 | (107-137) |

(107) (110) (120)
CysProLeuIleProGlySerThrThrThrSerThrGlyPro
(130) (137)
CysLysThrCysThrThrProAlaGlnGlyAsnSerMetPheProSerCys

FIG. 2

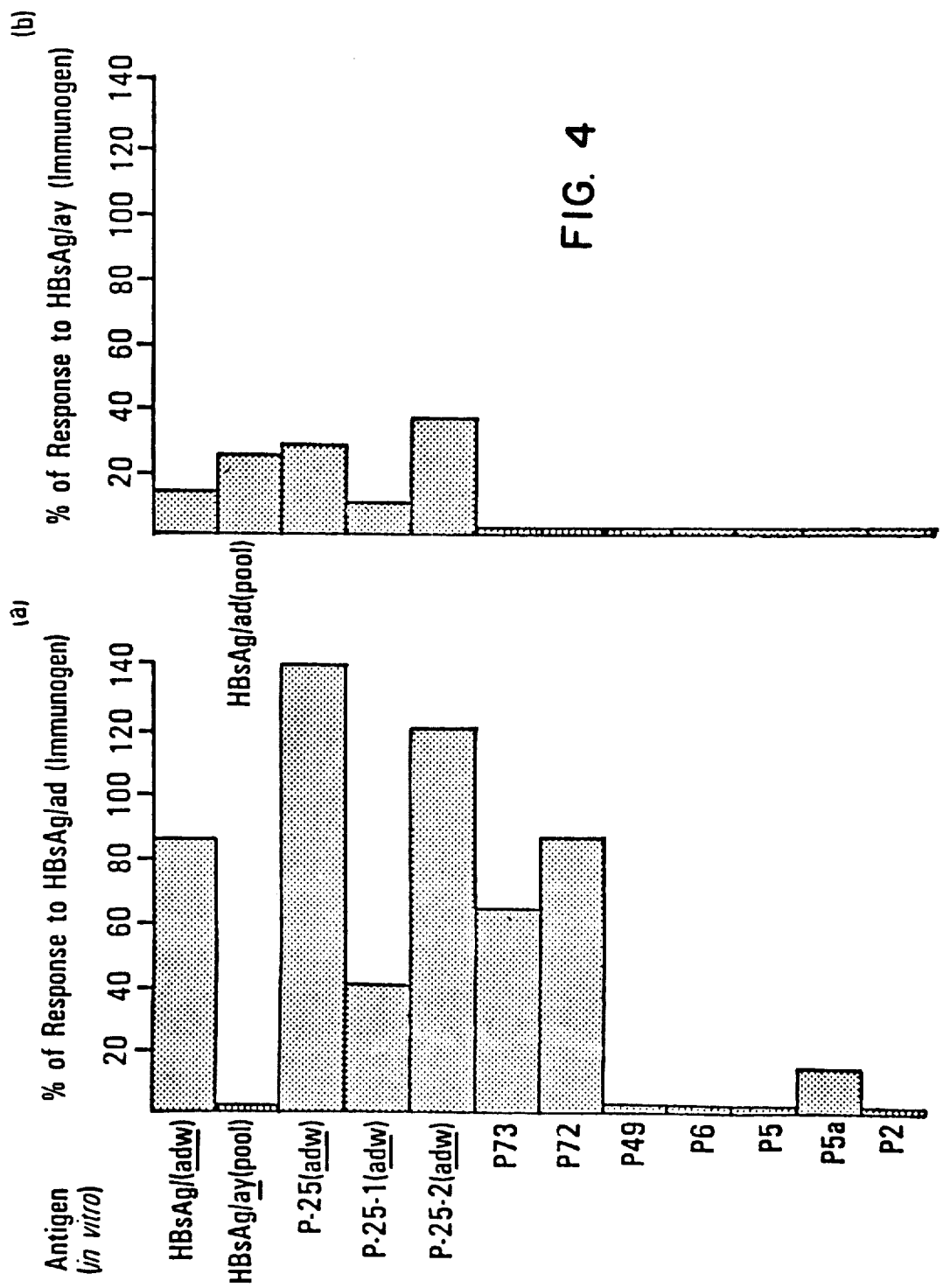

SYNTHETIC HEPATITIS B VIRUS VACCINE INCLUDING BOTH T CELL AND B CELL DETERMINANTS

DESCRIPTION

The U.S. Government has rights in this invention pursuant to grants awarded by the National Institutes of Health.

1. Technical Field

The present invention relates to chemically synthesized polypeptides having amino acid residue sequences that substantially correspond to the amino acid residue sequences of T cell and B cell determinant portions of a natural, pathogen-related protein, in particular, a hepatitis B virus surface antigen (HBsAg). When administered to a host alone, as polymers or as carrier-bound conjugates, the polypeptides induce the proliferation of thymus-derived cells in hosts primed against hepatitis B virus.

2. Background

The present invention relates to the production of novel synthetic antigens based upon information derived from DNA and/or protein sequences and to the use of those antigens in the production of vaccines, diagnostic reagents, and the like. More specifically, this invention relates to synthetic antigenic polypeptides, which when used alone, as a polymer or upon coupling to a carrier, immunologically correspond to a T cell and B cell determinant portion of hepatitis B virus surface antigen (HBsAg).

Viral hepatitis continues to rank as one of the most important unconquered diseases of mankind. The general term, viral hepatitis, refers principally to hepatitis A (infectious hepatitis) and to hepatitis B (serum hepatitis), although other known viruses such as yellow fever virus, Epstein-Barr virus and cytomegalovirus can cause hepatitis in man. Hepatitis is particularly known for its focal attack on the liver (Greek, hepar), but the disease also influences other organs.

In 1965, Blumberg discovered an antigen circulating in the blood of certain human beings [*J. Am. Med. Assoc.*, 191, 541 (1965) and *Ann. Int. Med.*, 66, 924 (1967)]. This substance was subsequently found by Prince to be the surface antigen of hepatitis B virus (HBsAg) that is produced in abundance by individuals who are chronically infected with the agent [*Proc. Natl. Acad. Sci. (USA)*, 60, 814 (1968)].

HBsAg has been the subject of extensive immunochemical characterization. Serologic studies show that several strains of the hepatitis B virus (HBV) have one or more determinants in common, which is designated a. Each strain also has two other determinants: either d or y and either w or r. Thus, there are four possible types of the virus: adw, ayw, adr and ayr. The specificity of HBsAg is associated with a single polypeptide [Gold et al., *J. Immunol.*, 117, 1404 (1976) and Shih et al., *J. Immunol.*, 120, 520 (1978)], the entire 226 amino acid sequence of which is established from the nucleotide sequence of the S gene [Tiollais et al., *Science*, 213, 406 (1981)] of HBV [Valenzuela et al., *Nature* (London), 280, 815 (1979); Galibert et al., *Nature* (London), 281, 646 (1979) and Pasek et al., *Nature* (London), 282, 575 (1979)].

There is an urgent need for a hepatitis B vaccine for groups which are at an increased risk of acquiring this infection. These groups include health care and laboratory personnel, and individuals requiring (1) maintenance hemodialysis; (2) repeated blood transfusions or the administration of blood products; (3) treatment with immunosuppressive or cytotoxic drugs and (4) treatment for malignant diseases and disorders associated with depression of the immune response. In addition, a vaccine is needed for individuals living in certain tropical areas where hepatitis B infection is prevalent.

Hepatitis A and B viruses, however, do not multiply significantly in cell culture, and there is no current source of laboratory propagated virus for vaccine preparation. Indeed, there has been a repeated failure to transmit hepatitis B virus (HBV) serially in tissue or organ cultures which has hampered progress towards the development of a conventional vaccine [Zuckerman, *Amer. J. Med. Sci.*, 270, 205 (1975)].

Classically, a vaccine is manufactured by introducing a killed or attenuated organism into the host along with suitable adjuvants to initiate the normal immune response to the organism while, desirably, avoiding the pathogenic effects of the organism in the host. That approach suffers from several well known limitations. These vaccines are complex and include not only the antigenic determinant of interest but many related and unrelated deleterious materials, any number of which may, in some or all individuals, induce an undesirable reaction in the host.

For example, vaccines produced in the classical way may include competing antigens which are detrimental to the desired immune response, antigens which include unrelated immune responses, nucleic acids from the organism or culture, endotoxins and constituents of unknown composition and source. These vaccines, generated from complex materials, inherently have a relatively high probability of inducing competing responses even from the antigen of interest.

In the past, antigens have been obtained by several methods including derivation from natural materials, coupling of a hapten to a carrier and by recombinant DNA technology. Sela et al. [*Proc. Nat. Acad. Sci. (USA)*, 68, 1450 (1971); *Science*, 166, 1365 (1969); and *Adv. Immun.*, 5, 129 (1966)] have also described certain synthetic antigens.

Certain "synthetic" antigens have been prepared by coupling small molecules (for example, dinitrophenol) to carriers (such as bovine serum albumin), thus producing antigens which cause the production of antibody to the coupled small molecule. The carrier molecule is often necessary because the small molecule itself may not be "recognized" by the immune system of the animal into which it is injected. This technique has also been employed in isolated instances to prepare antigens by coupling polypeptide fragments of known proteins to carriers, as described in the above-referenced Sela et al articles.

While this hapten-carrier technique has served the research community well in its investigations of the nature of the immune response, it has not been of significant use in the production of antigens which would play a role in diagnostic or therapeutic modalities. One reason for that deficiency is that to select and construct a useful antigenic determinant from a pathogen (e.g., hepatitis B virus) by this technique, one must determine the entire protein sequence of the pathogen to have a reasonable chance of success. Because of the difficulty of this task, it has rarely, if ever, been done.

Recombinant DNA technology has opened new approaches to vaccine technology and has the advantage that the manufacture begins with a monospecific gene; however, much of this advantage is lost in actual production of antigen in E. coli, or other organisms. In this procedure, the gene material is introduced into a plasmid which is then introduced into E. coli which produces the desired protein, along with other products of the metabolism, all in mixture with the nutrient. This approach is complicated by the uncertainty as to whether the desired protein will be expressed in the transformed E. coli.

Moreover, even though the desired protein may be produced, there is uncertainty as to whether or not the protein can be harvested or whether it will be destroyed in the process of E. coli growth. It is well known, for example, that foreign or altered proteins are digested by E. coli. Even if the protein is present in sufficient quantities to be of interest, it must still be separated from all of the other products of the E. coli metabolism, including such deleterious substances as undesired proteins, endotoxins, nucleic acids, genes and unknown or unpredictable substances.

Finally, even if it were possible (or becomes possible through advanced, though necessarily very expensive, techniques) to separate the desired protein from all other products of E. coli metabolism, the vaccine still comprises an entire protein which may include undesirable antigenic determinants, some of which are known to initiate adverse responses. Indeed, it is known that certain proteins which could otherwise be considered as vaccines include an antigenic determinant which induces serious cross reference or side reactions that prevent the use of the material as a vaccine.

It is also possible, using hybridoma technology, to produce antibodies to viral gene products. Basically, hybridoma technology allows one to begin with a complex mixture of antigens and to produce monospecific antibodies later in the process. In contrast, the present invention is the reverse process, in that we start with a relatively high purity antigenic determinant and thus avoid the necessity for purification of the desired antigenic product.

Hybridoma antibodies are known to exhibit low avidity and low binding constants, and therefore, have limited value. Moreover, in hybridoma technology, one must rely on the production of the antibody by cells which are malignant, with all of the attendant concerns regarding separation techniques, purity and safety.

Hybridoma production relies upon tissue culture or introduction into mice, with the obvious result that production is costly and there is an inherent variability from lot to lot.

In addition, it is difficult to make hybridomas that secrete antibodies to molecules which comprise only a small percentage of the complex mixture with which one must start, or which are poorly immunogenic and are overshadowed by stronger, dominant antigens.

Previous studies by Arnon et al., Proc. Nat. Acad. Sci. (USA), 68, 1450 (1971), Atassi, Immunochemistry, 12, 423 (1975) and Vyas et al. Science, 178, 1300 (1972) have been interpreted by those authors to indicate that short linear amino acid sequences are, in general, unlikely to elicit antibodies reactive with the native protein structure. It was thought that for most regions of most molecules, antigenic determinants resulted from amino acid residues well separated in the linear sequence but close together in the folded protein. The exact three dimensional conformation of the polypeptides used to elicit antibodies was thought to be critical in most cases, even for those antigens involving amino acids close together in a sequence.

For example, Sela thought it necessary to synthesize a rather elaborate loop structure to elicit an anti-lysozyme response. Atassi engineered many elaborate molecules, each intended to mimic the tertiary structure of the target protein. And Vyas concluded that the three dimensional conformation of hepatitis B surface antigen was a critical factor in eliciting antibodies reactive with that native structure.

Sutcliffe et al., Nature, 287, 801 (1980) discovered that antibodies to linear polypeptides react with native molecules, and recent investigations have shown that relatively short chemically synthesized polypeptides can elicit antibodies reactive with almost any region of an exposed surface of a protein [Green et al., Cell, 28, 477 (1982)]. Moreover, since amino-acid sequences can now be determined rapidly with nucleic acid sequencing technology, synthetic polypeptides can be synthesized to make vaccines of a precision not previously possible. Thus, elaborate biosyntheses are unnecessary, uneconomical and obsolete.

U.S. Pat. No. 4,415,491 to Vyas discloses a series of peptides that correspond to the a determinant of hepatitis B virus surface antigen. Although no data is presented concerning the protection of a host, the peptides are described as being useful in a hepatitis vaccine preparation.

Current vaccines for HBV consist of subviral components of the virus surface coat (HBsAg) purified from the plasma of chronically HBV-infected donors and inactivated [McAuliffe et al., Rev. Infect. Dis., 2, 470 (1980)]. Clinical trials have demonstrated the safety and efficacy of current HBsAg vaccines but such vaccines are limited in supply and are relatively expensive, particularly for those countries with the highest incidence of HBV disease. Chemically synthesized polypeptides, therefore, offer considerable advantages in terms of cost and safety of HBV vaccination programs.

It is known that antisera to synthetic polypeptides predicted from the nucleotide sequence of various regions of the S gene of HBV react with native HBsAg by radioimmunoprecipitation [Lerner et al., Proc. Natl. Acad. Sci. (USA), 78, 3403 (1981)] and commercial solid-phase radioimmunoassays for anti-HBsAg [Gerin et al., in Viral Hepatitis, Szmuness et al (eds.), 49–55 (1982)].

It has been recently determined that a pathogen-related protein can be immunologically mimicked by the production of a synthetic polypeptide whose sequence corresponds to that of a determinant domain of the pathogen-related protein. Such findings are reported by Sutcliffe et al., Nature, 287, 801 (1980) and Lerner et al., Proc. Natl. Acad. Sci. (USA), 78, 3403 (1981).

Moreover, Gerin et al., Proc. Natl. Acad. Sci. (USA), 80, 2365 (1983) have recently shown limited protection from hepatitis B virus upon immunization with carrier bound-synthetic polypeptides having amino acid sequences that correspond to the amino acid sequence of a determinant portion of HBsAg; in particular, residues 110–137.

The construction of a synthetic HBsAg vaccine, however, may require in addition to synthetic polypeptides corresponding to B cell (antibody-producing) epitopes, synthetic polypeptides corresponding to non-overlapping T cell determinants.

By way of further background, three cellular components of the immune system are B cells (bursa- or bone marrow-derived lymphocytes), T cells (thymus-derived lymphocytes) and macrophages. B cells circulate in the blood and the lymph fluid and are involved in the production of antibodies. T cells amplify or suppress the response by B cells.

Macrophages, on the other hand, are involved in presenting and concentrating antigens to B and T cells. Moreover, macrophages secrete several biologically active mediators that regulate the type and magnitude of both T and B cell responses either by enhancing or suppressing cell division or differentiation. Macrophages are nonspecific and react against any foreign antigen. T and B cell, however, are antigen-specific and react via cell membrane receptors that are specific for the particular antigen.

In mice, the in vivo antibody production to HBsAg is regulated by at least 2 immune response (Ir) genes, one in the I-A subregion (Ir-HBs-1) and one in the I-C subregion (Ir-HBs-2) of the murine H-2 complex. It is observed that immunization with a chemically synthesized peptide corresponding to the d̲ determinant did not distinguish between high and non-responder murine strains. Milich et al., *J. Immunol.*, 130, 1401 (1983). This suggests that Ir-restriction may occur through T cell recognition of additional, perhaps nonoverlapping, regions of the molecule.

The linkage between major histocompatibility complex and the regulation of immune responsiveness to HBsAg in mice has been extended to the human immune response by the report of an association between HLA-DR phenotype and nonresponsiveness to a recent trial HBsAg vaccine. Thus, the construction of synthetic HBsAg vaccine may require, in addition to B cell epitopes, a sufficient diversity of T cell determinants to accommodate the genetic variation in epitope recognition of an outbred human population.

The following information would be very valuable in developing a synthetic HBsAg vaccine: (1) whether synthetic peptide fragments representing a highly restricted region of the native HBsAg (i.e., about 6 amino acids) can induce a T cell proliferative response, which, as with native HBsAg, is regulated by H-2 linked genes; (2) whether T cell recognition sites overlap with antibody binding sites; (3) whether multiple T cell recognition sites exist on HBsAg and if so whether the site(s) recognized depend on the H-2 genotype of the responding strain; (4) whether the T cell site(s) recognized determine the specificity and quality of the humoral response; and (5) whether human HBsAg-primed T cells are activated by the same determinants that induce T cell proliferation in mice.

BRIEF SUMMARY OF THE INVENTION

The present invention relates to certain synthetic polypeptides that have special characteristics and properties, and to products and methods utilizing those synthetic polypeptides.

Throughout this application, the terms "peptide" and "polypeptide" are used interchangeably. As used herein, the term "synthetic polypeptide" means a chemically built-up, as compared to a biologically built and degraded, chain of amino acid residues that is free of naturally occurring proteins and fragments thereof. Such synthetic polypeptides can induce the production of anti-polypeptide antibodies in a host.

A synthetic polypeptide in accordance with this invention has an amino acid residue sequence that is shorter than that of hepatitis B virus surface antigen but includes an amino acid residue sequence that corresponds immunologically to that of at least one determinant portion of hepatitis B virus surface antigen (HBsAg).

The polypeptide, when used alone, as a polymer (synthetic multimer) or bound to a carrier such as keyhole limpet hemocyanin (KLH) or the like as a conjugate and introduced in an effective amount as a vaccine in a physiologically tolerable diluent such as water, saline and/or an adjuvant into a host animal, can induce the production of antibodies and the proliferation of thymus-derived cells in the host.

The vaccine is prepared by providing one or more of the following polypeptides, a polymer thereof or a carrier-bound conjugate thereof and dissolving or dispersing an effective amount of the polypeptide in a physiologically tolerable diluent.

Preferred sequences of synthetic polypeptides, for use in a vaccine, comprise amino acid residue sequences (or a portion thereof) of B cell determinant portions of HBsAg (also referred to herein as B cell-stimulating and priming portions) taken from left to right and in the direction from the amino-terminus to the carboxy-terminus including:

| | |
|---|---|
| (110) | (120) |
| Phe(Ile)ProGlySerSer(Thr)ThrThrSerThrGlyProCys | |
| | (130) |
| Arg(Lys)ThrCysMet(Thr)ThrThr(Pro)AlaGlnGly | |
| | (137) |
| Thr(Asn)SerMetTyr(Phe)ProSerCys; | |
| (125) | (130) |
| Met(Thr)ThrThr(Pro)AlaGlnGlyThr(Asn)SerMet | |
| | (137) |
| Tyr(Phe)ProSerCys; and | |
| (107) | (110) |
| CysProLeuPhe(Ile)ProGlySerSer(Thr)ThrThrSerThr | |
| (120) | |
| GlyProCysArg(Lys)ThrCysMet(Thr)ThrThr(Pro)Ala | |
| (130) | (137) |
| GlnGlyThr(Asn)SerMetTyr(Phe)ProSerCys | |

GlnGlyThr(Asn)SerMetTyr(Phe)ProSerCys
wherein each amino acid residue in parentheses is an alternative to the immediately preceding amino acid residue, and the numerals in parentheses above particular amino acid residues in the above sequences identify positions of the particular amino acid residue relative to the amino-terminus of the hepatitis B virus surface protein. Such polypeptides induce the production of antibodies that can immunoreact with hepatitis B virus and protect a host from infection.

Preferred sequences of synthetic polypeptides, for use in a vaccine, also include an amino acid residue sequence (or a portion thereof) of a T cell determinant portion of HBsAg that induces T cells to proliferate (also referred to herein as a T cell-proliferating portion) taken from left to right and in the direction from the amino-terminus to the carboxy-terminus as follows:

| | | |
|---|---|---|
| (140) | (150) | (154) |
| ThrLysProSerAspGlyAsnCysThrCysIleProIleProSer | | | wherein the numbers in parentheses above particular amino acid residues in the above sequence identify positions of the particular amino acid residue relative to the amino-terminus of the hepatitis B virus surface protein.

In addition, vaccine according to the present invention, against infection by hepatitis B virus can include an effective amount of a synthetic polypeptide having an amino acid residue sequence that immunologically corresponds substantially to an amino acid residue sequence of a natural pathogen-related protein encoded by a hepatitis B virus from about positions 107 to 154, 110 to 154 or 125 to 154 from the amino-terminus thereof, and a physiologically tolerable diluent. The vaccine, when introduced into a host, is capable of inducing the production of antibodies and the proliferation of thymus-derived cells in the host. Such antibodies can immunoreact with hepatitis B virus and the vaccine can protect the host from hepatitis B viral infection.

For example, the synthetic polypeptide can include the sequence of amino acid residues taken from left to right and in the direction from amino-terminus to carboxy-terminus, and represented by the formula:

Phe(Ile)ProGlySerSer(Thr)ThrThrSerThrGly
ProCysArg(Lys)ThrCysMet(Thr)ThrThr(Pro)Ala
GlnGlyThr(Asn)SerMetTyr(Phe)ProSerCysCysCys
ThrLysProSerAspGlyAsnCysThrCysIleProIle-
ProSer wherein each amino acid residue in parentheses is an alternative to the immediately preceding amino acid residue.

That sequence corresponds to positions 110 to 154 as shown in FIGS. 1 and 2. The amino acid residue sequences that correspond to positions 107 to 154 and to positions 125 to 154 are also shown in FIGS. 1 and 2.

Each of the above synthetic polypeptides can be used in a monomeric form alone or conjugated to a carrier molecule such as KLH or tetanus toxoid. The synthetic polypeptides can also be used in a multimeric form.

When utilized in multimermic form, each polypeptide is one of a plurality of repeating units of a multimer. In one embodiment, the multimer contains at least two of the polypeptides bonded together head-to-tail through an amide bond formed between the amine group of the amino-terminus of one polypeptide and the carboxyl group of the carboxy-terminus of the second polypeptide. In another multimeric embodiment, the polypeptide is one of a plurality of repeating units of a polymer whose polypeptide repeating units are bonded together by interpolypeptide cystine disulfide bonds formed between the Cys residues of the polypeptide repeating units.

In another embodiment, the present invention includes a diagnostic system for determining the presence of cell-mediated immune responsiveness to HBsAg and the presence of a hepatitis B virus antigen in a host comprising a synthetic polypeptide as described above that has an amino acid residue sequence that corresponds to the amino acid sequence of a T cell determinant of HBsAg. The polypeptide, when administered to a host intradermally in an effective amount and in physiologically tolerable diluent, is capable of inducing the proliferation of thymus-derived cells in the host. The proliferation is indicated by erythema (redness) and induration (hardening of the skin) at the site of intradermal administration.

Methods are also disclosed for inducing the proliferation of thymus-derived cells in a host previously immunized to hepatitis B virus and for determining the presence of a hepatitis B virus antigen in a host. The methods include the steps of providing a T-cell proliferating polypeptide as discussed herein and administering intradermally an effective amount of the polypeptide to the host in a physiologically tolerable diluent according to the latter method, the proliferation of thymus-derived cells and the presence of a hepatitis B virus antigen in the host is indicated by erythema and induration at the site of intradermal administration.

The present invention provides several advantages and benefits. One advantage of the present invention is that use of a synthetic polypeptide obviates the need for the presence of its corresponding intact protein. The polypeptide itself provides a vaccine sufficient to protect the host from disease. Consequently, impurities such as cellular debris and toxins that are associated with the production of usable amounts of viral proteins from bacteria are absent from the product of this invention.

Moreover, a synthetic hepatitis B virus vaccine having both B cell and T cell determinants obviates the need to select a carrier appropriate for use in humans to stimulate the proliferation of thymus-derived cells in the recipient.

Another benefit of the present invention is that antibodies in antisera raised to the synthetic polypeptide immunoreact with and can be used to detect the presence of antigenic proteins and polypeptides associated with hepatitis B virus.

Still further advantages and benefits of the present invention will become apparent to those skilled in the art from the detailed description, Examples and claims which follow.

BRIEF DESCRIPTION OF THE DRAWINGS

In the drawings, which constitute a portion of this disclosure:

FIG. 1 illustrates the 226 amino acid sequence of the HBsAg/ayw protein as translated by Pasek et al., Nature, 282, 575 (1979) from the nucleic acid sequence. Regions of the protein selected for synthesis according to the present invention are indicated by bold underlining. Residues that are not the same in the three published nucleotide sequence determinations are lightly underlined [Pasek et al., Id.; Valenzuela et al., Nature, 280, 815–819 (1979); and Galibert et al., Nature, 281, 646–650 (1979)]. The following single letter and three letter codes (See FIG. 2) correspond to the indicated amino acids—A, Ala (L-Alanine); C, Cys (L-Cysteine); D, Asp (L-Aspartic acid); E, Glu (L-Glutamic acid); F, Phe (L-Phenylalanine); G, Gly (Glycine); H, His (L-Histidine); I, Ile (L-Isoleucine); K, Lys (L-Lysine); L, Leu (L-Leucine); M, Met (L-Methionine); N, Asn (L-Asparagine); P, Pro (L-Proline); Q, Gln (L-Glutamine); R, Arg (L-Arginine); S, Ser (L-Serine); T, Thr (L-Threonine); V, Val (L-Valine); W, Trp (L-Tryptophan); and Y, Tyr (L-Tyrosine).

FIG. 2 illustrates the amino acid sequences of polypeptides designated 1, 5, 5a, 6, 49, 49a, 72, 71, 72a and 73 using the conventional three letter code for each amino acid. These sequences are read from left to right and in the direction from the amino-terminus to the carboxy-terminus of the polypeptide. Polypeptides 1, 5, 5a and 6 correspond to residues 48–81, 38–52, 47–52 and 95–109, respectively, of HBsAg. Polypeptides 49 and 72 correspond to residues 110–137 of HBsAg (peptide 73 corresponds to residues 107–137) as predicted from the S gene nucleotide sequence of HBV DNA from an ayw donor (polypeptide 49) [Galibert et al., Nature (London), 281, 646–650 (1979)]and an adw donor (polypeptide 72 and 73) [Valenzuela et al., Nature (London), 280, 815–819 (1979)]. The underlined residues in polypeptides 72 and 73 indicate positions of amino acid variability between those sequences and that of polypeptide 49.

Figure 3:
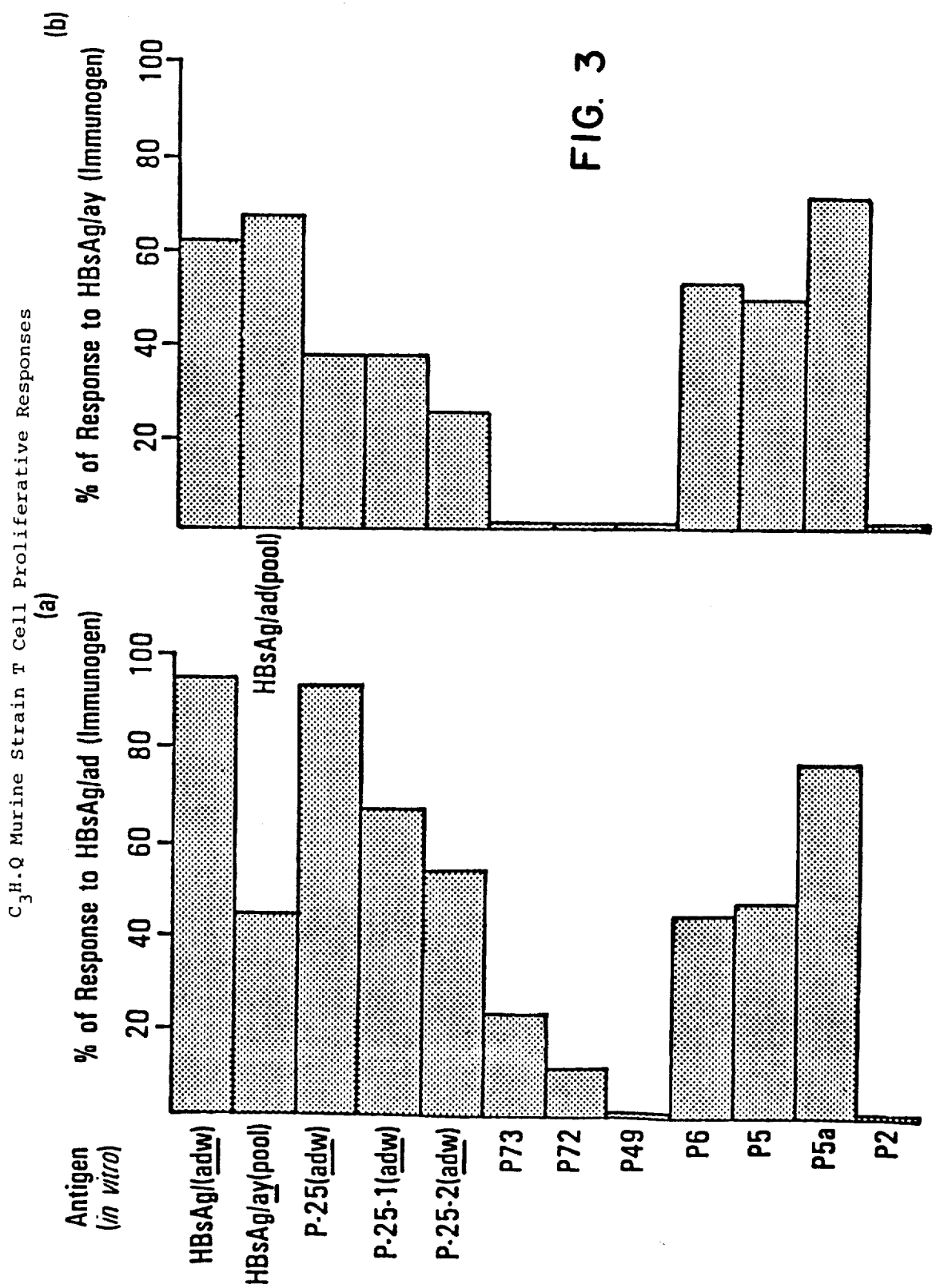

Polypeptides 49a and 72a consist of the C-terminal 12 amino acids of polypeptides 49 and 72, respectively (residues 125-137). Polypeptide 71 corresponds to residues 140 to 154 of HBsAg.

FIG. 3 illustrates the mouse C₃H.Q strain T cell proliferative responses in popliteal lymph node cells primed by HBsAg (ad or ay subtype) induced in vitro by: native HBsAg; P25 (the 1-226 residue subunit of HBsAg); the following tryptic fragments of P25: P25-1 (residues 1-122) and P25-2 (residues 123-226), and P73, P72, P49, P6, P5, P5a and P2 (residues 140-148). As used herein, the letter "P" before a number means "peptide" or "polypeptide". Proliferation was determined by incorporation of tritiated thymidine ($^3$HTdR) into cellular DNA, and was expressed as a percent response elicited by the immunogen. The immunogen HBsAg/ad elicited a proliferation which produced 20,477 counts per minute (cpm) and the immunogen HBsAg/ay elicited a proliferation which produced 33,000 cpm.

FIG. 4 illustrates the mouse B10.A strain T cell proliferative responses induced by: native HBsAg, P25 (the 1-226 residue); the following tryptic fragments of P25: P25-1 (residues 1-122) and P25-2 (residues 123-226); and P73, P72, P49, P6, P5, P5a and P2. Proliferative response doses and means of measurement were the same as in FIG. 3. The proliferative responses elicited by immunogens HBsAg/ad and HBsAg/ay were 8724 cpm and 11,444 cpm, respectively. Details of the assays of FIGS. 3 and 4 are provided in Sections IV and V.

DETAILED DESCRIPTION OF THE INVENTION

I. Introduction

Synthetic polypeptides having amino acid residue sequences that substantially correspond to the amino acid sequences of the d (P72) and y (P49) determinants of HBsAg have been synthesized by Lerner et al., *Proc. Natl. Acad. Sci. (USA)*, 78, 3403 (1981). These polypeptides possess the antigenic specificity of the native determinants as demonstrated by their ability to bind anti-native HBsAg antibodies. In addition, it has been demonstrated that immunization with P49 conjugated to keyhole limpet hemocyanin (KLH) induces a high-titered anti-y response in a murine inbred responder strain. Milich et al., *J. Immunol.*, 130, 1401 (1983).

However, immunization with free (unconjugated) P49 induces little or no anti-y production. Similarly, free P72 induces a very minimal anti-d response. Indeed, the reduced immunogenicity of unconjugated (relative to conjugated) synthetic peptide analogues of HBsAg has been encountered by numerous investigators.

Therefore, protein carrier molecules such as KLH and tetanus toxoid have been used as a means of providing nonspecific T cell helper function for these synthetic determinants.

In order to construct a synthetic HBsAg vaccine possessing both T cell and B cell determinants, it is first necessary to identify the T cell and B cell determinants of HBsAg.

It is known that the murine immune response to HBsAg is regulated by H-2-linked Ir genes, and that this regulation is expressed at the T cell level. Nonresponder haplotypes are characterized by a defect in T-helper cell function, whereas HBsAg-specific B cell repertoirs are intact. In addition to the reduced immunogenicity of free, unconjugated synthetic peptide analogues of HBsAg, immunization with P72 (residues 110-137) or P49 (residues 110-137) did not distinguish between high responder and nonresponder strains.

These results indicate that P72 and P49 represent B cell epitopes of the native structure, but lack the appropriate T cell determinants.

Thus, immunization with these B cell epitopes alone does not generate the necessary Ir-restricted, T cell helper function.

A number of HBsAg synthetic peptides were screened as described herein in an HBsAg-specific T cell proliferative assay in order to identify T cell determinants. Mice were immunized in vivo with native HBsAg/ad or HBsAg/ay, and popliteal lymph node (PLN) cells were harvested and challenged in vitro with either native HBsAg or a series of synthetic polypeptides.

Several polypeptides were identified that stimulate HBsAg-primed PLN cells to proliferate in vitro. In particular, polypeptides P5 (residues 38-52), P5a (residues 47-52), P6 (residues 95-109) and P71 (residues 140-154) of FIGS. 1 and 2 stimulate T cell proliferation of murine PLN cells primed in vivo with HBsAg of the ad or ay subtype.

Moreover, at least polypeptide P1 (residues 48-81) and polypeptide P5 induce T cell proliferation in human peripheral blood lymphocytes (PBL).

It should be noted that P1, P5, P5a, P6 and P71 do not induce the production of antibodies cross-reactive with native HBsAg nor do they bind native anti-HBs antibodies. Conversely, P72 and P49 do not induce (or at best induce only minimal) T cell proliferation, yet bind anti-HBs of the appropriate specificity, and provide some protection against hepatitis B disease.

These results indicate the existence of distinct loci for T cell and B cell determinants on the same HBsAg polypeptide. Use of a synthetic T cell determinant with a B cell determinant, preferably a synthetic B cell determinant, according to the present invention provides a potent synthetic antigen.

Previous genetic analysis of the immune responses to HBsAg in H-2 congenic, recombinant murine strains predicts the existence of a "carrier-determinant" on HBsAg, since a dominant influence on the immune response to all HBsAg determinants maps to a single Ir gene locus. Polypeptides 5, 5a and 6 correspond to such a carrier-determinant on the native molecule. These polypeptides function as intrinsic carriers and provide functional T cell help for any and all synthetic B cell epitopes to which they are coupled.

Thus, one aspect of the present invention is directed to vaccines that contain as an active ingredient an effective amount of a T cell-proliferating polypeptide described herein, e.g. at least one of polypeptides 1, 5, 5a and 6. Such a vaccine may be introduced into a host animal (or a human) after that animal has been immunized with (primed to) a HBsAg B cell activator such as the complete HBsAg molecule or polypeptides such as those denominated 49, 49a, 72 and 72a. More preferably, the T cell-proliferating polypeptide of this invention is administered to the host animal along with a priming, B cell-stimulating immunogen such as polypeptides 49, 49a, 72 and 72a.

The more preferred T cell-proliferating and B cell-stimulating and priming polypeptides may be introduced into the host as separate entities of one vaccine wherein each is linked to its own carrier or as a homopolymer of active polypeptide repeating units. More preferably, both types of polypeptide are linked to a single carrier and thereby constitute a single active entity in the vaccine. A synthetic HBsAg vaccine containing co-polymerized polypeptide repeating units with amino acid sequences that substantially correspond to amino acid sequences of T cell and also B cell determinants of the native molecule is clearly a still more preferred approach rather than attempting to select appropriate protein carrier molecule for immunization into human subjects.

Moreover, enhancement of the immunogenicity of synthetic polypeptides related to HBsAg is a fundamental aspect in the development of a synthetic HBsAg vaccine. The highly immunogenic synthetic HBsAg vaccine described herein has desirable medical as well as economic advantages as compared to the current human plasma-derived vaccines.

II. Discussion

The data from this study demonstrate that limited regions of the hepatitis B surface antigen (HBsAg) molecule; in particular, residues 48 to 81 (which correspond to synthetic peptide P1), residues 38 to 52 (which correspond to synthetic peptide P5), residues 95 to 109 (which correspond to synthetic peptide P6) and residues 47 to 52 (which correspond to synthetic peptide P5*a*) and residues 140 to 154 (which correspond to synthetic peptide 71) are sites that are preferentially recognized by HBsAg-primed T cells.

Although synthetic peptides P1, P5, P5*a*, P6 and P71 induce T cell proliferative responses, these peptides do not correspondingly induce or bind antibodies that recognize the native molecule. This illustrates the disparity in determinant specificity that can exist between B and T cells in response to complex protein antigens.

Such disparity has been observed in a variety of antigenic systems as described in the following references: Senyk et al., *J. Exp. Med.*, 133, 1294 (1971); Thomas et al., *J. Immunol.*, 126, 1095 (1981); Berkower et al., *Proc. Natl. Acad. Sci.* (*USA*), 79, 4723 (1982); Kipps et al., *J. Immunol.*, 124, 1344 (1980). In contrast, other investigators have demonstrated similar T and B cell receptor specificities for antigens as described in the following references: Twining et al., *Mol. Immunol.*, 18, 447 (1981); Rajewsky et al., *Eur. J. Immunol.*, 4, 111 (1974); Becker et al., *Eur. J. Immunol.*, 5, 262 (1975). Any assumption, however, that T and B cell recognition sites never or always overlap is therefore overly simplistic.

With reference to HBsAg, $C_3H.Q$ (H-$2^q$), or simply "$C_3H.Q$", and B10.T(6R)(H-$2^q$) or "B10.T(6R)", murine strains preferentially recognize the amino-terminal fragment of HBsAg [in particular, residues 1–122 of the P25 HBsAg polypeptide subunit (P25-1)] and the constituent peptides P5, P5*a* and P6. Murine strains $C_3H.Q$ and B10.T(6R) are referred to herein as "responder strains" or "high responder strains" based on the degree of the proliferative response.

The proliferative response of B10.A (H-$2^a$), or "B10.A", murine strain T cells, on the other hand, is directed almost exclusively to the carboxy-terminal fragment of HBsAg [specifically, residues 123–226 of P25 (P25-2)] and to the P72 synthetic peptide, which also serve as antibody binding sites on HBsAg. Murine strain B10.A is referred to as an "intermediate responder strain" because the proliferative response is less than that of $C_3H.Q$ or B10.T(6R).

Murine strain SJL (H-$2^S$) or "SJL" has been found to confer nonresponsiveness to immunization with HBsAg and, thus, is referred to as a "nonresponder strain".

Therefore, multiple T cell recognition sites appear to exist on HBsAg and the selective activation of T proliferating cells is dependent on the murine major histocompatibility complex (H-2) haplotype of the responding strain. A similar preferential selection of T cell epitopes in a hapten-carrier system controlled by I-region genes in the murine H-2 complex has been reported in Seman et al., *J. Immunol.*, 129, 2082 (1982).

The humoral anti-HBsAg response is regulated by at least two immune response (Ir) genes. One of the genes is in the I-A subregion (Ir-Hbs-1) and the other is in the I-C subregion (Ir-HBs-2) of the murine H-2 complex. The Ir-Hbs-1 regulates the response to all HBsAg determinants; whereas, the influence of the Ir-HBs-2 is subtype-specific. (For a general description of Ir genes and subregions see Bach, *Genetic Control of Immune Responses* in *Immunology*, ch. 24, pages 677–703 (John Wiley & Sons, New York 1982) which description is incorporated herein by reference).

In the strains used herein, a positive T cell proliferative response to the amino-terminal fragment of the HBsAg P25 polypeptide subunit P25-1 and to synthetic peptides P5*a* or P6 indicated an enhanced anti-HBs antibody production to all HBsAg determinants. In contrast, the T cell proliferative pattern of the B10.A murine strain corresponds to reduced primary anti-HBs antibody production which is limited to subtype specificity.

A site or sites on the amino-terminal fragment of synthetic peptides P5, P5*a* and P6 serves as a T cell "carrier-determinant" recognized by T helper cells capable of providing functional help to B cell clones specific for the a, d and y epitopes and restricted by the I-A subregion. In the absence of recognition of the "carrier-determinant," the influence of subtype-specific helper or suppressor T cells restricted by the I-C subregion is observed. Since the B10.A strain produces a minimal secondary anti-a antibody response, subtype-specific T cells may also provide help to B cell clones specific for the conformational a-epitope.

These observations have important implications in terms of the development of a synthetic HBsAg vaccine; especially in view of the possibility that human HBsAg-primed T cells may recognize the same epitopes as murine T cells.

In particular, the linkage between the major histocompatability complex and the regulation of immune responsiveness to HBsAg in mice has been extended to the human immune respone. Walker et al., *Proc. Amer. Assoc. Blood Banks*, 4 (1981) have reported an association between a particular phenotype at the DR gene locus of the human major histocompatibility complex (HLA-DR) and nonresponsiveness to a recent trial HBsAg vaccine.

Thus, the construction of a synthetic HBsAg vaccine preferably includes, in addition to B cell determinants, a sufficient diversity of T cell determinants to accommodate the genetic variation in epitope recognition of an outbred human population.

IV. Results

A. Identification of Murine B Cell Epitopes

The polypeptide sequences of hepatitis B surface antigen (HBsAg) that induce the production of and bind to murine anti-HBsAg antibodies were identified.

A number of polypeptide sequences of HBsAg group a subtype yw (HBsAg/ayw) were selected for synthetic polypeptide synthesis. These polypeptides are denominated P1, P2, P3, P4, P5, P5a, P6, P49, P49a, P72, P72a and P73 and are illustrated in FIG. 1.

The peptides were chemically synthesized by solid-phase methods as described herein in Section VI and as described in greater detail in Merrifield et al., *J. Am. Chem. Soc.*, 85, 2149 (1963) and Houghten et al., *Int. J. Peptide Protein Research*, 16, 311 (1980). Anti-polypeptide antibodies specific for each of the synthetic peptides were produced when the synthetic polypeptides were coupled to KLH and introduced into rabbits as a vaccine that also included water and an adjuvant.

Pooled purified preparations of HBsAg group a subtype d (HBsAg/ad) and HBsAg group a subtype y (HBsAg/ay) were obtained from Dr. Robert Louie (Cutter Laboratories, Berkeley, Calif.). The antibodies to the synthetic peptides were analyzed for reactivity to HBsAg/ad and HBsAg/ay by a hemagglutination assay (HA) as described herein. The ability of the solid-phase polypeptides to bind murine anti-native HBsAg antibodies of d or y specificity was also determined as described below.

Polypeptides P73 (residues 107-137), P72 (residues 110-137) and P72a (residues 125-137) induced the production of antibodies that were cross-reactive with native HBsAg of the ad subtype. Polypeptides P49 (residues 110-137) and P49a (125-137), on the other hand, induced the production of antibodies that were cross-reactive with native HBsAg primarily of the ay subtype. (See Table 1).

TABLE 1

Identification of B Cell Epitopes On Synthetic Peptide Analogues of HBsAg

| Peptide[1] | Anti-peptide reactivity With Native HBsAg HA Titer | | Anti-Native HBs Reactivity With Solid-Phase Peptides[2] RIA Titer | |
|---|---|---|---|---|
| | HBsAg/ad | HBsAg/ay | Anti-HBs/d[3] | Anti-HBS/y |
| P73 | 1:1280 | 1:40 | 1:512 | 1:32 |
| P72 | 1:160 | 0 | 1:1024 | 0 |
| P72a | 1:160 | 0 | ND[4] | ND |
| P49 | 1:80[5] | 1:160 | 1:32 | 1:128 |
| P49a | 0 | 1:160 | 0 | 1:64 |
| P6 | 0 | 0 | 0 | 0 |
| P5 | 0 | 0 | 1:8 | 0 |
| P5a | 0 | 0 | 0 | 0 |
| P4 | 0 | 0 | 1:4 | 0 |
| P3 | 0 | 0 | 1:16 | 1:8 |
| P2 | 0 | 0 | 0 | 0 |
| P1 | 0 | 0 | 1:16 | 0 |

[1]Anti-peptide antisera were produced in rabbits; and all peptides were conjugated to keyhole limpet hemocyanin (KLH) with the exception of P73, P72 and P1. Anti-peptide antisera prepared in mice [Milich et al., J. Immunol., 130, 1401 (1983)] and chimpanzees [Gerin et al., Proc. Natl. Acad. Sci. (USA), 80, 2365 (1983)] demonstrate the same specificities for native HBsAg.
[2]Peptides (5 micrograms per well) were adsorbed to polystyrene microtiter plates.
[3]Anti-HBs/d and y were produced by immunizing B10.S(9R) mice with HBsAg/ad or HBsAg/ay, respectively. This H-2 recombinant strain produces only a subtype-specific antibody response.
[4]ND = Not determined.
[5]Not specific for the common a determinant.

Polypeptides P72 and P72a correspond in amino acid residue positions to polypeptides P49 and P49a, but contain the amino acid substitutions shown in FIGS. 1 and 2. Although anti-P49 antibodies reacted with both subtypes of HBsAg, HA inhibition analysis demonstrated the cross-reactivity was not directed to the common "a"-determinant, but rather to a determinant present on the native HBsAg/ad, P49 and P72 but not on native HBsAg/ay.

In addition, the ability of the above series of synthetic polypeptides to bind murine anti-native HBsAg antibodies of d or y specificity was examined. As shown in Table 1, P72 bound anti-HBs/d but did not bind to anti-HBs/y; whereas P49 bound anti-HBs/y and anti-HBs/d to some extent (presumably through a cross-reactive determinant not related to the common a determinant). The fact that P49a induced the production anti-polypeptide antibody that reacted only with the ay subtype and bound anti-HBs/y but not anti-HBs/d demonstrates the y-specificity of this polypeptide. P73, which is identical to P72 with the addition of amino-terminal amino acids, demonstrated primarily d-specificity; however, in immunogenicity studies a small cross-reactive component was observed. It is interesting to note that HA inhibition analysis suggested this component was specific for a determinant common to both subtypes (i.e., anti-a). The remainder of the synthetic polypeptides used in this determination induced no anti-peptide antibody cross-reactive with HBsAg in non-denaturing conditions and did not bind or bound to a minimal extent anti-native HBsAg antibodies.

These results are in general agreement with those reported by Gerin et al., *Proc. Natl. Acad. Sci. (USA)*, 80, 2365 (1983) and confirm the localization of the d and y subtype-specific antibody binding sites within synthetic polypeptides P72a and P49a, respectively. These synthetic polypeptides correspond to residues 125-137 of the amino acid sequence of HBsAg, and although P49a differs from P72a at four residues, Peterson et al., *J. Biol. Chem.*, 257, 10414 (1982) have suggested that amino acid substitutions at residues 131 and 134 confer subtype-specificity.

The minor and low-titered reactivity of anti-native HBsAg with a number of the other synthetic polypeptides may result from the complexity of the antisera that most likely contain specificities directed to HBsAg degradation products. In support of this position, antisera to polypeptides P3, P4 and P6 do not react with native HBsAg, but nonetheless do bind denatured HBsAg [Lerner et al., *Proc. Natl. Acad. Sci. (USA)*, 78, 3403 (1981)]. The "a-like" activity of P73 may be explained by the addition of a cysteine residues to P72, since a cyclic form of a synthetic peptide corresponding to residues 122 through 137 produced by introduction of an intrachain disulphide bond has been reported to contain a conformation-dependent a epitope [Ionescu-Matlo et al., *J. Immunol.*, 130, 1947 (1983)].

B. Identification of Murine T Cell Epitopes

The polypeptide sequences of HBsAg that are recognized by native HBsAg primed mouse T cells were identified.

Native HBsAg/adw was purified from the plasma of a single chronic carrier as described in Peterson et al., *J. Biol. Chem.*, 256, 6975 (1981). P25, a polypeptide subunit of HBsAg, and two tryptic fragments of P25 designated P25-1 (residues 1-122) and P25-2 (residues 123-226) were prepared from the same HBsAg/adw positive donor by preparative polyacrylamide gel electrophoresis as also described in Peterson et al., supra. Synthetic peptides P73, P72, P49, P6, P5, P5a, P2 and P1 (see FIG. 1) were synthesized according to the methods described herein. These polypeptides and synthetic peptides were lyophilized, resuspended in culture media and were sterilized by gamma radiation (5000 rads).

Culture media used was original Click's Media [as described in Click et al., *Cell Immunol.*, 3, 264 (1972)] that was modified by the addition of ten millimolar HEPES [4(-2-hydroxyethyl)-1-piperazinethane-sulfonic acid] and ten micrograms per milliliter gentamycin and by the substitution of 0.5 percent syngenic normal mouse serum for fetal calf serum. The P25, P25-1 and P25-2 were not completely soluble in the culture media. The polypeptides and synthetic peptides suspended in culture media are referred to herein as antigens and were cultured with harvested popliteal lymph node (PLN) cells as described below.

C$_3$H.Q(H-2$^q$) is an inbred murine strain that produces early (10 days) IgG antibodies to both the common a subtype and the d/ determinants following immunization with HBsAg as described in Milich et al., *J. Immunol.*, 130, 1395 (1983). Groups of five C$_3$H.Q mice were immunized in the rear footpads with an emulsion of complete Freund's adjuvant (CFA) and sixteen micrograms of a pooled purified preparation of HBsAg/ad or HBsAg/ay (obtained as described earlier). Twelve days later popliteal lymph node (PLN) cells were harvested and cultured in vitro (2.5 × 10$^6$ cells per milliliter) with the antigens that were produced as described above.

The antigens were tested in culture over a dose range, however, the proliferative responses illustrated in FIG. 3 correspond to the following in vitro doses: native HBsAg (1.0 micrograms per milliliter); P25, P25-1, P25-2 (10 micrograms per milliliter); and synthetic peptides P73, P72, P49, P6, P5, P5a and P2 (100 micrograms per milliliter).

HBsAg specific proliferative response of PLN cells harvested up to 13 days post-immunization was due to proliferating T cells as described in Milich et al., *J. Immunol.*, 130, 1401 (1983). Consequently, unfractionated PLN cells were used in the determinations.

HBsAg specificity was demonstrated by the absence of antigen-induced proliferation in CFA-primed PLN T cells. Proliferation was determined by incorporation of tritiated thymidine ($^3$HTdR) into DNA and was expressed as a percent of the response elicited by the antigen. Assays were repeated on at least three separate occasions.

The T cell proliferative response is expressed as a percentage of that induced by the synthetic polypeptide. HBsAg/ad-primed PLN T cells from C$_3$H.Q mice responded in vitro to native HBsAg/adw almost as well as to the synthetic polypeptides used, and substantially less to native HBsAg/ay, which represents proliferation directed towards common group-specific determinant(s) (FIG. 3a).

Polypeptide P25 induced T cell proliferation to the same extent as the native HBsAg-adw from which it was prepared. Although micrograms per milliliter of P25 was required as compared to 1.0 microgram per milliliter of native antigen, the P25 preparation was not completely soluble in the culture media, and the effective dose may have been substantially less than 10 micrograms per milliliter. This is of interest since P25 binds anti-HBs antibody approximately 300-fold less efficiently than the native antigen.

P25-1 induced a better proliferative response than P25-2 (67 percent vs. 45 percent) at 10 micrograms per milliliter, and significantly greater proliferation at 2.5 micrograms per milliliter (53 percent vs. 13 percent). The superior proliferative response induced by P25-1 as compared to P25-2 in this strain was confirmed by the fact that synthetic polypeptides P73 and P72, constituents of P25-2, induced minimal proliferative responses; whereas P6 (residues 95–109), P5 (38–52) and P5a (47–52), constituents of P25-1, induced significant proliferation in HBsAg/ad-primed mice (FIG. 3a). Induction of T cell proliferation by synthetic polypeptides required a 100-fold excess on a weight basis and a 10$^4$-fold excess on a molar basis as compared to native HBsAg.

It should be emphasized that P6, P5 and P5a do not induce the production of antibodies cross-reactive with native HBsAg nor do they bind native anti-HBs, and conversely, P73 and P72 induce only minimal T cell proliferation in C$_3$H.Q mice, yet induce and bind anti-HBs/d (See Table 1). These results indicate the existence of distinct T cell and B cell determinants on the same HBsAg polypeptide. Polypeptide P5a, although only 6 amino acids in length, induced a greater degree of T cell proliferation than did polypeptide P5. This may be because P5a is derived from an extremely hydrophilic region of the amino-terminal fragment (P25-1) of HBsAg and is considerably more soluble in saline than is polypeptide P5. As previously discussed, the other large hydrophilic portion of the polypeptide corresponds to the antibody binding regions primarily located on the carboxy-terminal fragment (P25-2).

To determine subtype-specificity of the T cell responses, C$_3$H.Q mice were also primed in vivo with HBsAg of the ay subtype. The proliferative responses to native HBsAg of the ad subtype and to the adw-derived P25 and tryptic fragments P25-1 and P25-2 were reduced as compared to HBsAg/ad-primed mice. However, the responses to synthetic polypeptides P6, P5 and P5a were virtually equivalent to the responses induced after HBsAg/ad priming (FIG. 3b). Polypeptides P73 and P72 were not stimulatory for HBsAg/ay-primed T cells, and P49 did not induce a proliferative response after priming with either subtype of HBsAg.

These results indicate that P73 and P72 represent subtype-specific determinants at the T cell and the B cell level. P6, P5 and P5a, on the other hand, represent common T cell recognition sites present on both subtypes. This is consistent with the amino acid sequence, since the P6 and P5a regions are invariable in the HBsAg sequences determined to date, whereas, the P72 region is variable and amino acid substitutions in this region dictate subtype-specificity. Gerin et al., *Proc. Natl. Acad. Sci. (USA)*, 80, 2365 (1983) and Lerner et al., *Proc. Natl. Acad. Sci. (USA)*, 78, 3403 (1981). The HBsAg-specificity of these responses was demonstrated by the absence of proliferation in CFA-primed PLN T cells in response to HBsAg and its related fragments.

Polypeptide 71

The ability of polypeptide P71 (residues 140–154) to stimulate or induce the proliferation of thymus-derived cells in hosts primed against HBsAg was also investigated. Murine strain C$_3$H.Q was immunized with HBsAg subtype ad and HBsAg subtype ay. Mice of a nonresponder murine strain (SJL) were inoculated with HBsAg subtype ad. (See Table 2).

TABLE 2

| Murine Strain | Primed T cells | Tritiated Thymidine [$^3$HTdR] Incorporation ($\Delta$ cpm)[1] polypeptide 71 (micrograms/milliliter) | | | | | | |
|---|---|---|---|---|---|---|---|---|
| | | 100 | 50 | 25 | 12 | 3 | 0.07 | 0.03 |
| C$_3$H.Q | HBsAg/ad | — | — | 20,299 | 20,331 | 15,007 | 6,832 | 3,179 |

TABLE 2-continued

| Murine Strain | Primed T cells | Tritiated Thymidine [$^3$HTdR] Incorporation ($\Delta$ cpm)[1] polypeptide 71 (micrograms/milliliter) | | | | | | |
|---|---|---|---|---|---|---|---|---|
| | | 100 | 50 | 25 | 12 | 3 | 0.07 | 0.03 |
| C$_3$H.Q | HBsAg/ay | 8,130 | 9,694 | 11,490 | — | — | — | — |
| SJL | HBsAg/ad | 0 | 0 | 0 | 0 | 0 | 0 | 0 |

[1]The change in counts per minute (cpm) after correction for background readings from the control media.

Immunizations were performed as described in Milich et al., *J. Immunol.*, 130, 1395 (1983). Groups of five C$_3$H.Q mice were immunized in the rear footpads with an emulsion of complete Freund's adjuvant and sixteen micrograms of a pooled purified preparation of HBsAg-/ad or HBsAG/ay (obtained as described earlier). Twelve days later popliteal lymph node (PLN) cells were harvested and cultured in vitro (2.5×10$^6$ cells per milliliter) in the previously described modified Click's media and in the presence of polypeptide P71.

As indicated in Table 2, P71 was used in culture over a dose range of 0.03 to 100 micrograms P71 per milliliter of solution. HBsAg specificity was demonstrated by the absence of antigen-induced proliferation in the CFA-primed PLN T cells. Proliferation was determined by the incorporation of tritiated thymidine ($^3$HTdR) into DNA as described hereinafter in greater detail.

Note that polypeptide P71 has no measurable effect on nonresponder SJL HBsAg-primed T cells. The data presented in Table 2, however, indicate that P71 can act as a T cell determinant on the carboxy-terminal region of the native HBsAg molecule. This is consistent with the ability of P25-2 (residues 123-266) to induce T cell proliferation in each of the responder strains studied.

C. Determination of the Role of H-2 Restriction in Mouse T Cell Recognition Sites B10.A is an inbred murine strain which only produces an anti-HBsAg-d/ subtype specific response after primary immunization as described in Milich et al., *J. Exp. Med.*, 159, 41 (1984) which is incorporatred herein by reference. Groups of 5 B10.A mice were primed in vivo with either HBSAg/ad or HBsAg/ay. See FIG. 4. The immunization protocol, culture conditions and preparation, concentration of in vitro antigens, and T cell proliferative testing are the same as described above in section B.

Since the high responder C$_3$H.Q strain preferentially recognizes P25-1, P6 and P5 at the T cell level and produces high titered anti-HBs/a and anti-HBs/d or y after primary immunization, it was of interest to examine T cell responses to these antigens in an intermediate responder strain which only produces subtype-specific anti-HBs/d or y after primary immunization. The B10.A strain respresnts such a strain.

B10.A PLN T cells primed with HBsAg/ad responded to native HBsAg/ad but not at all to native HBsAg/ay (FIG. 3a). Although P25 was stimulatory for B10.A HBsAg/ad-primed PLN T cells, the responses to the tryptic fragments P25-1 and P25-2 indicated a preferential response to P25-2 rather than P25-1 in contrast to the C$_3$H.Q strain. Correspondingly, polypeptides P73 and P72 induced significant proliferation, whereas polypeptides P6, P5 and P5a were virtually non-stimulatory for B10.A PLN T cells primed with native HBsAg/ad or HBs/ay (FIG. 3b).

B10.A mice primed with HBsAg/ay demonstrated only minimal T cell proliferative response in HBsAg-/ay-primed mice (FIG. 3a).

These results demonstrate that B10.A HBsAg-primed T cells preferentially recognize the subtype-specific regions of the polypeptide (P25-2 and P72) rather than the group-specific regions as in the case of C$_3$H.Q murine strain. The ability of P72 to stimulate a d-specific proliferative response and induce and bind anti-native HBs/d clearly indicates that region 110-137 is recognized by both T cells and B cells in B10.A mice.

To determine the relevance of the above findings to peptide immunogenicity and in vivo anti-HBs antibody production, C$_3$H.Q and B10.A mice were immunized with P72, an analogue of the d determinant, and serum anti-peptide and anti-HBs titers were measured temporally.

As shown in Table 3, following primary immunization with native HBsAg/ad the C$_3$H.Q strain produced subtype and group-specific anti-HBs. The B10.A strain produced only anti-HBs/d, and to a lesser degree than the C$_3$H.Q strain. However, following tertiary immunization with P72 the B10.A strain produced a 32-fold greater anti-P72 response and a 20-fold higher anti HBs/d response as compared to the C$_3$H.Q strain (Table 3).

TABLE 3

Strain-Dependent In vivo Antibody Production Following Immunization With Synthetic Peptide P72

| Strain | Immunogen[1] | Serum Anti-Polypeptide P72 and Anti-HBs Titers (RIA)[2] | | |
|---|---|---|---|---|
| | | Anti-P72 | Anti-HBs/ad | Anti-HBs/ay |
| C$_3$H.Q | HBsAg/ad (1°) | — | 1:2,560 | 1:320 |
| | P72 (1°) | 0 | 0 | 0 |
| | P72 (2°) | 1:640 | 1:8 | 0 |
| | P72 (3°) | 1:640 | 1:8 | 0 |
| B10.A | HBsAg/ad (1°) | — | 1:320 | 0 |
| | P72 (1°) | 1:160 | 0 | 0 |
| | P72 (2°) | 1:2,560 | 1:20 | 0 |
| | P72 (3°) | 1:20,480 | 1:160 | 0 |

[1]Groups of 6 mice were immunized with 4.0 micrograms of native HBsAg/ad or 100 micrograms of peptide P72 in CFA intraperitoneally. Peptide recipient mice were given identical secondary (2°) tertiary (3°) immunizations at 2-week and 4-week intervals, respectively.
[2]Pooled serum antibody titers were measured by solid-phase radioimmunoassay (RIA) and expressed as the highest serum dilution to yield twice the counts of the preimmunization sera.

It should be noted that C$_3$H.Q mice immunized with P72 conjugated to a carrier protein produced vigorous anti-P72 and anti-HBs/d responses. Reduced immunogenicity of P72 in the C$_3$H.Q strain is consistent with the inability of P72 to induce a T cell proliferative response in HBsAg/ad-primed C$_3$H.Q mice. These results illustrate that the high responder status of the C$_3$H.Q strain is not mediated through T cell recognition of the subtype-specific d determinant as represented by P72. In contrast, the B10.A strain, which demonstrates P72-induced T cell proliferation following HBsAg/ad immunization, was capable of responding to P72 immunization with the production of significant concentrations of anti-P72 and anti-HBs/d antibodies. Therefore, the immunogenicity of synthetic peptide analogues of HBsAg is dependent on the requirement for both T cell and B cell determinants; and the recognition of the T cell determinant is dictated by the H-2 genotype of the responding murine strain.

D. Determination of Synthetic Peptides That Elicit HBsAg-Specific T Cell Proliferation in Mice and are Recognized by Human Vaccine Recipient HBsAg Primed T Cells Peripheral blood lymphocytes from two human HBsAg/ad vaccine recipients (Haptavax, Merck & Co., Rahway, NJ) designated "DM" and "PW" and an unimmunized volunteer designated "CL" were compared for T cell responsiveness to native HBsAg/ad, native HBsAg/ay, and a series of synthetic peptide analogues of HBsAg.

As shown in Table 4, peripheral blood lymphocytes from one HBsAg vaccine recipient (DM) responded to native HBsAg of both subtypes and to polypeptides P72 and P5. However, the responses elicited by native HBsAg/ad and by polypeptide P72 were significantly greater than those elicited by native HBsAg/ay and by polypeptide P5 in terms of stimulation index and dose response.

In contrast, PBL from (PW) responded equally well to both native HBsAg subtypes, and correspondingly polypeptides P1 (residues 48–81) and P5 induced proliferative responses, whereas polypeptide 72 did not. The other synthetic peptides tested were not stimulatory nor did any of the antigens stimulate PBL obtained from the nonimmunized control (CL).

Similar to the findings of the murine model, at least two patterns of T cell specificity were observed in human responses. One pattern is characteristic of T cell recognition of distinct determinants (P1 and P5), which do not induce the production of or bind to anti-HBs antibodies. The other pattern involves recognition by T cells of a subtype-specific region that may overlap with B cell determinants.

between 6 and 12 weeks of age at the initiation of the studies were used in all studies.

Pooled preparations of HBsAg/ad and HBsAg/ay were provided by Dr. Robert Louie (Cutter Laboratories, Berkeley, Calif.). These preparations were purified by Cutter Laboratories from human plasma by a combination of standard procedures including ultracentrifugation, ammonium sulfate precipitation, pepsin digestion and gel chromatography. The HBsAg preparations were free of contaminating human serum proteins as tested by Ouchterlony analysis and immunoelectrophoresis versus goat anti-human serum [Milich et al., J. Immunol., 129, 320 (1982) which is incorporated herein by reference].

Native HBsAg/adw was purified from the plasma of a single chronic carrier donor by methods previously described by Peterson et al., J. Biol. Chem., 256, 6975 (1981). The structural polypeptide (P-25) and the tryptic fragments P-25-1 (residues 1–122) and P-25-2 (residues 123–226) were prepared from this same HBsAg-/adw positive donor by preparative polyacrylamide gel electrophoresis also as described by Peterson et al., supra. The synthetic peptides shown in FIG. 1 were synthesized by the solid-phase methods described herein. The polypeptides and tryptic fragments were lyophilized, resuspended in culture media as previously described and were sterilized by gamma irradiation (5000 rads).

B. Immunization

Anti-polypeptide antibodies were produced in rabbits. Polypeptides were coupled to keyhole limpet hemocyanin (KLH) through the existent or added cysteine of the polypeptide by using m-maleimidobenzoyl-N-hydroxysuccinimide ester (MBS) as the coupling reagent [See Section VI(c)]. Rabbits were immunized with polypeptide-KLH conjugates according to the following schedule: (1) 200 micrograms of polypeptide in complete Freund's adjuvant (CFA) administered subcutaneously on day 0; (2) 200 micrograms of polypeptide in incomplete Freund's adjuvant (IFA) on day 14; and

TABLE 4

| | | | | | | | | | | | | | |
|---|---|---|---|---|---|---|---|---|---|---|---|---|---|
| | PBL[1] Proliferative Responses of Human HBsAg Vaccine Recipients Challenged In Vitro With Synthetic Peptide Analogues And Native HBsAg | | | | | | | | | | | | |
| | Anti-HBs status (HA Titer) | | | PBL Proliferative Responses ($^3$H—TdR; CPM and SI)[2] | | | | | | | | | |
| HBsAg/adw | | | | In Vitro | | Antigens[3] | | | | | | | |
| Vaccine | HBsAg/ad | HBsAg/ay | Media | HBsAg/ad | HBsAg/ay | P72 | P49 | P6 | P5 | P3 | P2 | P1 | |
| (DM) + | 1:1600 | 1:800 | 3100 | 31,794 (10.3) | 20,656 (6.7) | 45,776 (14.8) | 3376 (1.1) | 5583 (1.8) | 11,648 (3.8) | 4442 (1.4) | 5320 (1.7) | 3500 (1.1) | |
| (PW) + | 1:8,192 | 1:1024 | 5000 | 14,665 (3.0) | 16,958 (3.4) | 6325 (1.3) | 6330 (1.3) | 4784 (0.9) | 10,500 (2.1) | 5683 (1.1) | ND | 22,102 (4.4) | |
| (CL) − | 0 | 0 | 2475 | 2426 (1.0) | 3638 (1.5) | 3069 (1.2) | 2723 (1.1) | 2277 (0.9) | 3316 (1.3) | ND[4] | ND | 2000 (0.8) | |

[1]PBL = Peripheral blood lymphocytes.
[2]Human proliferative responses were measured using peripheral blood lymphoycytes (PBL) and culture conditions modified from the murine assay as described in Leroux-Roels et al., (in press). The $^3$H—TdR incorporation is expressed as counts per minute (CPM) and stimulation index (SI). A stimulation index is the ratio of the stimulation induced by the test antigen (measured as counts per minute) to the stimulation induced by the control media (also measured as counts per minute).
[3]Antigens were used over a wide dose range; proliferative responses to 1.0 microgram per milliliter of native HBsAg and 100.0 micrograms per milliliter of peptide analogues are shown. Underscored responses were greater than two times the media control through at least four-fold dilutions.
[4]ND = Not Determined.

V. Materials and Methods
A. Materials

The C$_3$HQ, B10.A and SJL inbred murine strains and New Zealand white rabbits were obtained from the Research Institute of Scripps Clinic, La Jolla, Calif. The B10.T(6R) strain was provided by Dr. Hugh McDevitt (Stanford University, Palo Alto, Calif.). Female mice (3) 200 micrograms of polypeptide with 4 milligrams alum administered intraperitoneally on days 21 and 91. The animals were bled 15 weeks after the first injection. Polypeptides 1, 72 and 73 were injected without KLH. The above weights of the polypeptides do not include the weights of the carriers.

To study in vivo antibody production in mice, groups of mice were immunized with 4.0 micrograms native HBsAg/ad or 100 micrograms p72 in CFA by intraperitoneal injection. Peptide recipient mice were given identical secondary and tertiary immunizations at 2 Week and 4 week intervals. In vivo priming for the lymph node proliferative assay was accomplished by injection of a total of 16.0 micrograms HBsAg in CFA in a volume of 80 microliters into the two hind footpads of the recipient mice.

C. Measurement of anti-HBs.

Anti-HBs antibodies induced by immunization with a synthetic polypeptide or native HBsAg and anti-polypeptide antibodies induced by polypeptide immunization were measured by two methods. Murine sera were evaluated for anti-HBs and anti-polypeptide reactivity in an indirect, immunoglobulin class-specific, radioimmunoasay (RIA) utilizing solid-phase HBsAg (ad or ay subtype) or synthetic peptides, goat anti-mouse IgG, and were developed with $^{125}$I-labeled, swine anti-goat Ig as described in Milich et al., *J. Immunol.*, 129, 320 (1982).

To analyze rabbit sera for anti-HBs activity, a hemagglutination (HA) system was used. Human type 'O', Rh negative red blood cells were coated with HBsAg (ad or ay subtype) by the chromic chloride method as described in Vyas et al., *Science*, 170, 332 (1970) which is incorporated herein by reference. The coated cells were added to 0.25 milliliters of serially diluted test sera in microtiter 'V'-bottom plates. All anti-HBs assays were performed in 5–10 percent normal human sera to neutralize any possible antibodies to contaminating human plasma proteins that may not have been removed from the HBsAg preparation by the purification procedures utilized.

D. Lymph node proliferation assay.

Groups of 5 mice were immunized in the hind footpads with an emulsion of CFA and 16 micrograms HBsAg (ad or ay subtype). Twelve days later popliteal lymph node (PLN) cells were harvested and cultured in vitro to a concentration of $5 \times 10^5$ cells with various challenge antigens. The in vitro antigens included native HBsAg [ad (pooled), ay (pooled) or adw from a single donor]; polypeptide P25; tryptic fragments P-25-1 and P-25-2; and a synthetic polypeptide of the present invention (P73, P72, P71, P49, P6, P5, P5a, P2, P1).

Draining popliteal lymph node cells were aseptically removed from each mouse and teased to yield a single cell suspension. The cells were washed twice with a balanced salt solution (BSS) containing phosphate-buffered saline (pH 7.2). The cells were resuspended in Click's medium containing BSS, L-glutamine, sodium pyruvate, antibiotics, 2-mercaptoethanol, essential and non-essential amino acids and vitamins. [See Click et al., *Cell Immunol.*, 3, 264 (1972).] Click's medium, was however modified by the addition of 10 millimolar HEPES (N-2-hydroxyethyl piperazine-N'-2-ethanesulfonic acid) and gentamycin (10 micrograms per milliliter) and by the substitution of 0.5 percent syngeneic normal mouse serum for fetal calf serum.

The antigens were tested in culture over a dose range. However, the proliferative responses shown in FIGS. 3 and 4 correspond to the following in vitro doses: native 100 micrograms per milliliter.

Viable lymph node cells ($4 \times 10^5$) in 0.1 milliliter of medium were placed in flat-bottom microtiter wells (Falcon 3072, Falcon Plastics, Inc.) with: (a) 0.1 ml. of HBsAg of the ad or ay subtype (2.0 to 0.6 micrograms per milliliter), (b) culture medium and ovalbimin (200 micrograms per milliliter as a negative control, or (c) purified protein derivative (PPD-50 micrograms per milliliter) as a positive control.

Cultures were incubated for 5 days at 37 degrees C. in a humidified atmosphere containing 5 percent carbon dioxide in air.

On the fourth day, each culture was pulsed with microcurie $^3$H-thymidine ($^3$HTdR) (6.7 Ci/millimole, New England Nuclear, Boston, MA) 16 to 18 hours before harvesting. Proliferation was determined by the incorporation of $^3$HTdR into DNA. Specific proliferation as a stimulation index (SI) that equals the counts per minute (cpm) of the test antigen divided by the cpm of the media control. It was demonstrated previously that the HBsAg-specific proliferation response of draining PLN cells harvested up to 13 days post-immunization is due to proliferating T cells [Milich et al., *J. Immunol*, 130, 1401 (1983)]. Therefore, unfractionated PLN cells were used in experiments reported herein.

VI. Peptide Syntheses and Selection

A. Synthesis of Polypeptides

The polypeptides of this invention were chemically synthesized by solid-phase methods as described in Merrifield et al., *J. Am. Chem. Soc.*, 85, 2149 (1963) and Houghten et al., *Int. J. Peptide Protein Research*, 16, 311 (1980). The relatively short polypeptides used herein substantially correspond to antigenic determinants of HBsAg.

FIG. 1 shows the 226 amino acid residue sequence of HBsAg. The amino acid residue sequences of the preferred synthetic polypeptides described herein are shown in FIGS. 1 and 2. In certain instances, a cysteine residue was added to the amino-terminus or to the carboxy-terminus of some of the polypeptides to assist in coupling to a protein carrier as described below. The compositions of all polypeptides were confirmed by amino acid analysis.

Generally, an immunogen or synthetic polypeptide is made by the steps of providing a plurality of amino acids that correspond to the amino acid residues of an antigenic determinant domain of HBsAg and synthesizing those amino acids into a polypeptide that has a peptide sequence corresponding to the peptide sequence of that antigenic determinant. The produced synthetic polypeptide can be used to produce a vaccine, usually by linking it to a carrier to form a conjugate and then dispersing an effective amount of the conjugate in a physiologically tolerable diluent.

The polypeptides are preferably synthesized according to the above-referenced solid phase methods using a cysteine resin. See Merrifield et al., supra. The side chains on individual amino acids are protected as follows: Arg-tosyl, Ser-, Thr-, Glu- and Asp-O-benzyl; Tyr-O-bromobenzyloxy carbamyl; Trp-N-formyl. The N-formyl group on the Trp residues is removed after cleavage of the peptide from the resin support by treatment with 1.0 molar ammonium bicarbonate at a peptide concentration of 1.0 milligram/milliliter for 16 hours at the room temperature. Yamashiro et al., *J. Org. Chem.*, 38, 2594–2597 (1973). The efficiency of coupling at each step can be monitored with ninhydrin or picric acid and is preferably greater than 99 percent in all cases. See Gisin, *Anal. Chem. Acta*, 58, 248–249 (1972) and Kaiser, *Anal. Biochem.*, 34, 595–598 (1980).

Throughout the application, the phrase "immunologically corresponds substantially" in its various grammatical forms is used herein and in the claims in relation to polypeptide sequences to mean that the polypeptide sequence described induces production of antibodies that bind to the polypeptide and (a) bind to the antigenic determinant of native HBsAg for polypeptides 49, 49a, 72 and 72a or (b) induce T cell proliferation for polypeptides 1, 5, 5a, 6 and 71. Thus, the peptides of this invention function immunologically as do the corresponding portions of the HBsAg molecules while also being capable of inducing the production of antibodies to themselves.

The term "substantially corresponds" in its various grammatical forms is used herein and in the claims in relation to polypeptide sequences to mean the polypeptide sequence described plus or minus up to three amino acid residues at either or both of the amino- and carboxy-termini and containing only conservative substitutions in particular amino acid residues along the polypeptide sequence.

The term "conservative substitution" as used above is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to designate those amino acid residues that normally either bear no charge or normally bear a charge, respectively, at physiological pH values. Exemplary nonionic residues include Thr and Gln, while exemplary ionic residues include Arg and Asp.

The word "antigen" has been used historically to designate an entity that is bound by an antibody and to designate the entity that induces the production of the antibody. More current usage limits the meaning of antigen to that entity bound by an antibody, while the word "immunogen" is used for the entity that induces antibody production. In some instances, the antigen and immunogen are the same entity as where a synthetic polypeptide is utilized to induce production of antibodies that bind to the polypeptide. However, the same polypeptide (P49a) can also be utilized to induce antibodies that bind to a whole protein such as HBsAg, in which case the polypeptide is both immunogen and antigen, while the HBsAg is an antigen. Where an entity discussed herein is both immunogenic and antigenic, it will generally be termed an antigen.

B. Preparation of Polymers

The polypeptides of the present invention can be connected together to form an antigenic polymer (synthetic multimer) comprising a plurality of the polypeptide repeating units. Such a polymer has the advantages of increased immunological reaction and where different polypeptides are used to make up the polymer, the additional ability to induce antibodies that immunoreact with several antigenic determinants of HBsAg.

A polymer (synthetic multimer) can be prepared by synthesizing the polypeptides as discussed above and by adding cysteine residues at both the amino- and carboxy-termini to form a "diCys-terminated" polypeptide. Thereafter, in a typical laboratory preparation, 10 milligrams of the diCys polypeptide (containing cysteine residues in un-oxidized form) are dissolved in 250 milliliters of 0.1 molar ammonium bicarbonate buffer. The dissolved diCys-terminated polypeptide is then air oxidized by stirring the resulting solution gently for a period of about 18 hours, or until there is no detectable free mercaptan by the Ellman test. [See Ellman, *Arch. Biochem. Biophys.*, 82, 70 (1959).]

The polymer (synthetic multimer) so prepared contains a plurality of the polypeptides of this invention as repeating units. Those polypeptide repeating units are bonded together by oxidized cysteine residues.

C. Coupling of Polypeptides to Protein Carriers

The synthetic polypeptides were coupled to keyhole limpet hemocyanin (KLH) or tetanus toxoid (TT) by either of the following two methods. In the first method, the carrier was activated with m-maleimidobenzoyl-N-hydroxysuccinimide ester and was subsequently coupled to the polypeptide through a cysteine residue added to the amino- or carboxy-terminus of the polypeptide, as described in Liu et al., *Biochem.*, 80, 690 (1979). In the second method, the polypeptide was coupled to the carrier through free amino groups, using a 0.04 percent glutaraldehyde solution as is well known. See, for example, Klipstein et al., *J. Inpect. Disc.*, 147, 318 (1983).

As discussed before, cysteine residues added at the amino- and/or carboxy-terminii of the synthetic polypeptide have been found to be particularly useful for forming conjugates via disulfide bonds and Michael addition reaction products, but other methods well known in the art for preparing conjugates can also be used. Exemplary additional binding procedures include the use of dialdehydes such as glutaraldehyde (discussed above) and the like, or the use of carbodiimide technology as in the use of a water-soluble carbodiimide, e.g. 1-ethyl-3-(3-dimethylaminopropyl) carbodiimide, to form amide links to the carrier.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

As is also well known in the art, it is often beneficial to bind the synthetic polypeptide to its carrier by means of an intermediate, linking group. As noted above, glutaraldehyde is one such linking group. However, when cysteine is used, the intermediate linking group is preferably an m-maleimidobenzoyl N-hydroxysuccinimide ester (MBS). MBS is typically first added to the carrier by an ester-amide interchange reaction. Thereafter, the above Michael reaction can be followed, or the addition can be followed by addition of a blocked mercapto group such as thiolacetic acid ($CH_3COSH$) across the maleimido-double bond. After cleavage of the acyl blocking group, and a disulfide bond is formed between the deblocked linking group mercaptan and the mercaptan of the added cysteine residue of the synthetic polypeptide.

The choice of carrier is more dependent upon the ultimate intended use of the antigen than upon the determinant portion of the antigen, and is based upon criteria not particularly involved in the present invention. For example, if a vaccine is to be used in animals, a carrier that does not generate an untoward reaction in the particular animal should be selected. If a vaccine is to be used in man, then the overriding concerns involve the lack of immunochemical or other side reaction of the carrier and/or the resulting antigen, safety and efficacy--the same considerations that apply to any vaccine intended for human use.

VII. Immunization Procedures

The inocula or vaccines used herein contain an effective amount of polypeptide alone, as a polymer of individual polypeptides linked together through oxidized cysteine residues or as a conjugate linked to a carrier. The effective amount of polypeptide per inoculation depends, among other things, on the species of animal inoculated, the body weight of the animal and the chosen inoculation regimen as is well known. Vaccines are typically prepared from the dried solid polypeptide or polypeptide polymer by suspending the polypeptide or polypeptide polymer in water, saline or adjuvant, or by binding the polypeptide to a carrier and suspending the carrier-bound polypeptide (conjugate) in a similar physiologically tolerable diluent such as an adjuvant (as previously described).

These inocula typically contain polypeptide concentrations of about 20 micrograms to about 500 milligrams per inoculation. The stated amounts of polypeptide refer to the weight of polypeptide without the weight of a carrier, when a carrier was used.

The vaccines also contained a physiologically tolerable (acceptable) diluent such as water, phosphate-buffered saline or saline, and further typically include an adjuvant. Adjuvants such as complete Freund's adjuvant (CFA), incomplete Freund's adjuvant (IFA) and alum are materials well known in the art, and are available commercially from several sources.

Vaccine stock solutions were prepared with CFA, IFA or alum as follows: An amount of the synthetic polypeptide, polymeric polypeptide or conjugate sufficient to provide the desired amount of polypeptide per inoculation was dissolved in phosphate-buffered saline (PBS) at a pH value of 7.2. Equal volumes of CFA, IFA or alum were then mixed with the polypeptide solution to provide a vaccine containing polypeptide, water and adjuvant in which the water-to-oil ratio was about 1:1. The mixture was thereafter homogenized to provide the vaccine stock solution.

Rabbits were injected subcutaneously and intraperitoneally, as previously described, with a vaccine comprising 200 to 400 micrograms of a polypeptide conjugate emulsified in complete Freund's adjuvant (CFA), incomplete Freund's adjuvant (IFA) or alum (5 milligrams per milliliter in each instance) on days 0, 14 and 21, respectively. Each inoculation (immunization) consisted of four injections of the inoculum. Mice were immunized in a similar way using one tenth of the above dose per injection.

Animals were bled 7 and 14 days after the last injection. In some cases, the animals received booster injections in alum, and were bled thereafter as necessary. Control pre-immune serum was obtained from each animal by bleeding just before the initial immunization.

Inoculum stock solutions can also be prepared with keyhole limpet hemocyanin (KLH), KLH in IFA (incomplete Freund's adjuvant), KLH-alum absorbed, KLH-alum absorbed-pertussis, edestin, thyroglobulin, tetanus toxoid, tetanus toxoid in IFA, cholera toxoid and cholera toxoid in IFA.

Upon injection or other introduction of the antigen or vaccine into the host, the immune system of the host responds by producing large amounts of antibody to the antigen. Since the specific antigenic determinant of the manufactured antigen, i.e., the antigen formed from the synthetic polypeptide and the carrier immunologically corresponds substantially to the determinant of the natural antigen of interest, the host becomes immune to the natural antigen. In the case where the invention is used as a vaccine, this is the desired result.

VIII. Delayed-Type Hypersensitivity (Skin Reaction Test)

The previously described diagnostic systems and assays are based on in vitro assays. Although particular steps of the assays can be carried out in vivo, the actual immune response is measured in tissue culture. The present invention, however, can also be applied to diagnostic systems involving the in vivo measurement of T cell responses. One example of such a system is a delayed-type hypersensitivity (DTH) reaction or what is more commonly known as a skin reaction test.

A DTH reaction can only occur in an individual previously exposed (sensitized) to a given antigen. The first exposure of an individual to the antigen produces no visible change, but the immune status of the individual is altered in that hypersensitivity to renewed exposure to that antigen results. Thus, upon intradermal or subcutaneous injection of the antigen (preferably in a buffered saline solution) a characteristic skin lesion develops at the injection site—a lesion that would not develop after a first antigen exposure. Because the response to the second (or challenge) antigen inoculum is typically delayed by 24 to 48 hours, the reaction is referred to as delayed-type hypersensitivity.

In humans, exposure to a sensitizing antigen takes place upon contact with the microorganism responsible for the disease (e.g., tuberculin from *Mycobacterium tuberculosis*, typhoidin from *Salmonella typhi* and abortin from *Brucella abortus*), and sensitization occurs as a result of a chronic infection. In animals, sensitization can be achieved by inoculation of an antigen emulsified in water, saline or an adjuvant.

In both humans and animals, hypersensitivity is tested in vivo by the injection of the antigen dissolved in a physiologically tolerable diluent such as saline solution into the skin (either intradermally or subcutaneously). DTH is usually a more sensitive diagnostic assay than the determination or measurement of the amount of antibody produced to an antigen. For example, only minute amounts of protein (a few hundred micrograms) are necessary for DTH sensitization of a mouse, while a much larger dose is needed to induce antibody production.

Since the polypeptides of the present invention (in particular, polypeptide P71) stimulate the proliferation of human and murine T cells following immunization (sensitization) with active HBsAg or with polypeptides 49, 49a, 72 and 72a, a skin reaction test was developed using one or more of the present synthetic polypeptides as a challenge antigen.

Selected murine strains are immunized with native HBsAg emulsified on an adjuvant such as complete Freund's adjuvant (CFA) by intradermal injection in the flank. In experimental situations, DTH sensitization usually occurs only when the sensitizing antigen is administered in adjuvant, preferably the complete type that includes bacilli of tuberculosis.

Seven days after immunization, the mice are challenged by intradermal inoculation in the ear or in the footpad with a predetermined amount of an antigen including (a) native HBsAg or (b) one or more of the present synthetic polypeptides in a known volume of phosphate-buffered saline (PBS). Control mice are inoculated intradermally with the same volume of PBS not including the antigen. Additional controls include mice immunized with only CFA.

Thickening of the tissue at the antigen-injection site relative to the control sites is evidence of a DTH reaction. Thus, the thickness of the ears and footpads is measured before challenge with the antigen and at 4, 24 and 48 hours after challenge.

Results demonstrate that the synthetic polypeptides of the present invention (in particular, P71) may be useful in an in vivo murine diagnostic system for the presence of a cell mediated immune response to HBsAg.

After the safety and effectiveness of the above polypeptides are shown in animal studies, the polypeptides can be used as challenge antigens in human skin reaction tests for recipients of HBsAg vaccines. The polypeptides are synthesized as previously described, purified by high pressure liquid chromatography (HPLC) techniques, sterilized and pyrogen-tested.

Since the T cell proliferative responses of human HBsAg vaccine recipients can be quite variable relative to polypeptide specificity, vaccine recipients and individuals serving as unvaccinated controls are challenged with a series of polypeptides. The kinetics and optimal antigen dose can be determined in the vaccine recipient group using the results from the animal studies as a guideline.

HBV acute and chronically infected individuals can also be studied for HBsAg-specific T cell sensitization using synthetic polypeptides as antigens for a skin reaction test.

In each instance, the challenge antigen is administered by intradermal injection of the particular polypeptide in a physiologically acceptable solution (about 1 milliliter) into the volar surface of the forearm. Use of a 25- or 27-gauge needle usually assures intradermal rather than subcutaneous administration of the antigen. Subcutaneous injection can lead to dilution of the antigen in tissues and can produce a false-negative test. The injection sites are then observed for erythema (skin reddening) and induration (swelling) at 4, 24 and 48 hours post-challenge.

The foregoing is intended as illustrative of the present invention but is not limiting. Numerous variations and modifications can be made without departing from the spirit and scope of the novel concepts of the invention. It should be understood that no limitation with respect to the specific compositions and uses described herein is intended or should be inferred.

What is claimed is:

1. A vaccine against infection by hepatitis B virus comprising:

(a) an effective amount of a synthetic polypeptide having an amino acid residue sequence taken from left to right and in the direction from amino-terminus to carboxy-terminus, and represented by the formula:

ThrLysProSerAspGlyAsnCysThrCysIleProIle-ProSer;

(b) an effective amount of at least one synthetic polypeptide having an amino acid residue sequence taken from left to right and in the direction from amino-terminus to carboxy-terminus selected from the group consisting of:

PheProGlySerSerThrThrSerThrGly-ProCysArgThrCys MetThrThrAlaGlnGlyThrSer-MetTyrProSerCys; MetThrThrAlaGlnGlyThrSer-MetTyrProSerCys; IleProGlySerThrThrThrSerThrGlyProCysLysThrCys ThrThrProAlaGln-GlyAsnSerMetPheProSerCys; ThrThrProAlaGln-GlyAsnSerMetPheProSerCys; and CysProLeuIle-ProGlySerThrThrThrSerThrGlyPro CysLysThrCysThrThrProAlaGlnGlyAsnSerMet PheProSer-Cys; and (c) a physiologically tolerable diluent, said vaccine when introduced into a host, being capable of inducing the production of antibodies and the proliferation of thymus-derived cells in the host, said antibodies immunoreacting with said hepatitis B virus, and said vaccine protecting the host from hepatitis B viral infection.

2. The vaccine according to claim 1 wherein said physiologically tolerable diluent is a member of the group consisting of water, saline and an adjuvant.

3. The vaccine according to claim 1 wherein said synthetic polypeptides are bound to a carrier.

4. The vaccine according to claim 1 wherein said carrier is selected from the group consisting of keyhole limpet hemocyanin, keyhole limpet hemocyanin in incomplete Freund's adjuvant, alum, keyhole limpet hemocyanin-alum absorbed, keyhole limpet hemocyanin-alum absorbed-pertussis, edestin, thyroglobulin, tetanus toxoid, tetanus toxoid in incomplete Freund's adjuvant, cholera toxoid and cholera toxoid in incomplete Freund's adjuvant.

5. A vaccine against infection by hepatitis B virus comprising an effective amount of a synthetic polypeptide having an amino acid residue sequence shorter than that of hepatitis B virus surface antigen that immunologically corresponds substantially to limited portions of an amino acid residue sequence of the hepatitis B virus surface antigen, said limited portions being (a) from about positions 140 to 154 and (b) from about positions 110 to 137 from the amino-terminus thereof, and a physiologically tolerable diluent, said vaccine when introduced into a host, being capable of inducing the production of antibodies and the proliferation of thymus-derived cells in the host, said antibodies immunoreacting with said hepatitis B virus and said vaccine protecting the host from hepatitis B viral infection.

6. The vaccine according to claim 5 wherein the synthetic polypeptide includes the sequences of amino acid residues taken from left to right and in the direction from amino-terminus to carboxy-terminus, and represented by the formulae:

ThrLysProSerAspGlyAsnCysThrCysIleProIle-ProSer; and Phe(Ile)ProGlySerSer(Thr)ThrThrSerThrGly ProCysArg(Lys)ThrCys-Met(Thr)ThrThr(Pro)Ala GlnGlyThr(Asn)SerMet-Tyr(Phe)ProSerCys wherein each amino acid residue in parentheses is an alternative to the immediately preceding amino acid residue.

7. A vaccine against infection by hepatitis B virus comprising an effective amount of a synthetic polypeptide having an amino acid residue sequence shorter than that of hepatitis B virus surface antigen that immunologically corresponds substantially to a limited portion of an amino acid residue sequence of a natural pathogen-related protein encoded by a hepatitis B virus surface antigen, said limited portion being from about positions 110 to 154 from the amino-terminus thereof, and a physiologically tolerable diluent, said vaccine when introduced into a host, being capable of inducing the production of antibodies and the proliferation of thymus-derived cells in the host, said antibodies immunoreacting with said hepatitis B virus and said vaccine protecting the host from hepatitis B viral infection.

8. The vaccine according to claim 7 wherein the synthetic polypeptide includes the sequence of amino acid residues taken from left to right and in the direction from amino-terminus to carboxy-terminus, and represented by the formula:

Phe(Ile)ProGlySerSer(Thr)ThrThrSerThrGly ProCysArg(Lys)ThrCysMet(Thr)ThrThr(Pro)Ala GlnGlyThr(Asn)SerMetTyr(Phe)ProSerCysCysCys ThrLysProSerAspGlyAsnCysThrCysIleProIleProSer wherein each amino acid residue in parentheses is an alternative to the immediately preceding amino acid residue.

9. A vaccine against infection by hepatitis B virus comprising an effective amount of a synthetic multimer in a physiologically tolerable diluent, said synthetic multimer comprising a plurality of polypeptide repeating units including (a) an amino acid residue sequence taken from left to right and in the direction from amino-terminus to carboxy-terminus, and represented by the formula: ThrLysProSerAspGlyAsnCysThrCysIleProIleProSer; and (b) at least one amino acid residue sequence taken from left to right and in the direction from amino-terminus to carboxy-terminus selected from the group consisting of:
PheProGlySerSerThrThrSerThrGly-ProCysArgThrCys MetThrThrAlaGlnGlyThrSer-MetTyrProSerCys; MetThrThrAlaGlnGlyThrSer-MetTyrProSerCys; IleProGlySerThrThrThrSerThrGlyProCysLysThrCys ThrThrProAlaGln-GlyAsnSerMetPheProSerCys; ThrThrProAlaGln-GlyAsnSerMetPheProSerCys; and CysProLeuIleProGlySerThrThrThrSerThrGlyPro CysLysThrCysThrThrProAlaGlnGlyAsnSerMet PheProSerCys;

wherein at least two Cys residues are present and said synthetic multimer contains at least one intramolecular cystine disulfide bond formed from at least two of the Cys residues present, said vaccine when introduced into a host, being capable of inducing the production of antibodies and the proliferation of thymus-derived cells in the host, said antibodies immunoreacting with said hepatitis B virus, and said vaccine protecting the host from hepatitis B viral infection.

10. The vaccine according to claim 9 wherein said physiologically tolerable diluent is a member of the group consisting of water, saline and an adjuvant.

11. The vaccine according to claim 9 wherein said synthetic multimer is bound to a carrier.

12. The vaccine according to claim 9 wherein said carrier is selected from the group consisting of keyhole limpet hemocyanin, keyhole limpet hemocyanin in incomplete Freund's adjuvant, alum, keyhole limpet hemocyanin-alum absorbed, keyhole limpet hemocyanin-alum absorbed-pertussis, edestin, thyroglobulin, tetanus toxoid, tetanus toxoid in incomplete Freund's adjuvant, cholera toxoid and cholera toxoid in incomplete Freund's adjuvant.

13. The vaccine according to claim 9 wherein the intramolecular cystine disulfide bond of said synthetic multimer is an intrapolypeptide disulfide bond.

14. The vaccine according to claim 9 wherein the polypeptide repeating units of said synthetic multimer are bonded together head-to-tail through an amide bond formed between the amine group of the amino-terminal residue of a first polypeptide repeating unit and the carboxyl group of the carboxy-terminal residue of a second polypeptide repeating unit.

15. The vaccine according to claim 14 wherein said synthetic multimer contains about two to about three of said polypeptide repeating units.

16. The vaccine according to claim 9 wherein the intramolecular cystine disulfide bond of said synthetic multimer is an interpolypeptide disulfide bond.

17. The vaccine according to claim 16 wherein the polypeptide repeating units of said synthetic multimer are bonded together by said interpolypeptide cystine disulfide bond formed between the Cys residues of said polypeptide.

18. A vaccine against infection by hepatitis B virus comprising a physiologically tolerable diluent having dispersed therein (i) an effective amount of a synthetic polypeptide having an amino acid residue sequence that immunologically corresponds substantially to a portion of an amino acid residue sequence of the hepatitis B virus surface antigen from about positions 110 to 137 from the amino-terminus thereof and (ii) an effective amount of a synthetic polypeptide having an amino acid residue sequence taken from left to right and in the direction from amino-teminus to carboxy-teminus, and represented by the formula:

ThrLysProSerAspGlyAsnCysThr CysIleProIleProSer;

said vaccine, when introduced into a host, being capable of inducing the production of antibodies and the proliferation of thymus-derived cells in the host, said antibodies immunoreacting with said hepatitis B virus and said vaccine protecting the host from hepatitis B viral infection.

19. A vaccine against infection by hepatitis B virus comprising a physiologically tolerable diluent having dispersed therein an effective amount of a synthetic polypeptide having an amino acid residue sequence taken from left to right and in the direction from amino-terminus to carboxy-terminus, and represented by the formula:

Phe(Ile)ProGlySerSer(Thr)ThrThrSerThr Gly-ProCysArg(Lys)ThrCysMet(Thr)ThrThr (Pro)AlaGlnGlyThr(Asn)SerMetTyr(Phe) ProSerCysCys-CysThrLysProSerAspGlyAsn CysThrCysIleProIleProSer, wherein each amino acid residue in parentheses is an alternative to the immediately preceding amino acid residue, said vaccine, when introduced into a host, being capable of inducing the production of antibodies and the proliferation of thymus-derived cells in the host, said antibodies immunoreacting with said hepatitis B virus and said vaccine protecting the host from hepatitis B viral infection.

* * * * *

UNITED STATES PATENT AND TRADEMARK OFFICE
CERTIFICATE OF CORRECTION

PATENT NO. : 4,599,230
DATED : July 8, 1986
INVENTOR(S) : David R. Milich et al.

It is certified that error appears in the above-identified patent and that said Letters Patent is hereby corrected as shown below:

Column 15, line 10, "$\underline{d}$/" should be --$\underline{d}$/$\underline{y}$--.

Column 17, line 41, "anti-HBsAg-$\underline{d}$/l" should be --anti-HBsAg-$\underline{d}$/$\underline{y}$--

Signed and Sealed this

Fourteenth Day of June, 1988

Attest:

DONALD J. QUIGG

Attesting Officer

Commissioner of Patents and Trademarks